(12) United States Patent
Beck et al.

(10) Patent No.: US 12,178,931 B2
(45) Date of Patent: Dec. 31, 2024

(54) CLEANING SYSTEM OF A MEDICAL IMAGING FACILITY

(71) Applicant: Siemens Healthcare GmbH, Erlangen (DE)

(72) Inventors: Thomas Beck, Dormitz (DE); Stefanie Gügel-Wild, Langensendelbach (DE); Marianne Köferl, Fichtelberg (DE); Bernd Maciejewski, Markt Bibart (DE); Michael Schneider, Bayern (DE); Annette Stein, Spardorf (DE); Philipp Höcht, Bavaria (DE); Sushant Mainali, Didcot (GB); Carina Moratz, Altdorf (DE); Tim Richter, Erlangen (DE); Martin Seifert, Bayreuth (DE)

(73) Assignee: Siemens Healthineers AG, Erlangen (DE)

( * ) Notice: Subject to any disclaimer, the term of this patent is extended or adjusted under 35 U.S.C. 154(b) by 541 days.

(21) Appl. No.: 17/534,691

(22) Filed: Nov. 24, 2021

(65) Prior Publication Data
US 2022/0160918 A1 May 26, 2022

(30) Foreign Application Priority Data
Nov. 25, 2020 (DE) .......................... 102020214808.2

(51) Int. Cl.
*G06V 10/40* (2022.01)
*A61B 6/04* (2006.01)
(Continued)

(52) U.S. Cl.
CPC .............. *A61L 2/24* (2013.01); *A61B 6/0407* (2013.01); *A61L 2/10* (2013.01); *A61L 2/28* (2013.01);
(Continued)

(58) Field of Classification Search
CPC ....... G01T 1/164; G01T 1/167; G01T 1/2914; G01T 7/00; G01T 7/08; G01T 1/2018;
(Continued)

(56) References Cited

U.S. PATENT DOCUMENTS

| 2010/0034349 | A1 | 2/2010 | Kraus et al. |
| 2013/0130227 | A1 | 5/2013 | Peltz et al. |

(Continued)

FOREIGN PATENT DOCUMENTS

| CN | 110058741 A | * | 7/2019 |
| DE | 102014201673 A1 | | 7/2015 |

(Continued)

OTHER PUBLICATIONS

Office Action dated Jun. 28, 2021 for German Patent Application No. 102020214808.2.

*Primary Examiner* — Quan M Hua
(74) *Attorney, Agent, or Firm* — Banner & Witcoff Ltd.

(57) ABSTRACT

Method for the operation of a cleaning system of a medical imaging facility, wherein the imaging facility has an outer useful surface exposed to contaminating effects of patients and/or operators. During a utilization phase for an examination procedure of a patient, sensor data of a sensor arrangement detecting at least a portion of the useful surface is acquired and by evaluation of the sensor data, a surface map having potentially contaminated regions of the useful surface is determined. During a cleaning phase following the utilization phase, cleaning information of the potentially contaminated regions are output to a cleaner and/or used for actuation of at least one cleaning apparatus of the imaging facility for targeted cleaning of the potentially contaminated regions.

22 Claims, 12 Drawing Sheets

(51) Int. Cl.
- *A61L 2/10* (2006.01)
- *A61L 2/24* (2006.01)
- *A61L 2/28* (2006.01)
- *G06T 7/00* (2017.01)
- *G06T 7/20* (2017.01)
- *G06T 7/60* (2017.01)
- *G10L 25/66* (2013.01)
- *H04N 13/254* (2018.01)

(52) U.S. Cl.
CPC ............ *G06T 7/0014* (2013.01); *G06T 7/20* (2013.01); *G06T 7/60* (2013.01); *G10L 25/66* (2013.01); *H04N 13/254* (2018.05); *A61L 2202/11* (2013.01); *A61L 2202/14* (2013.01); *A61L 2202/17* (2013.01); *A61L 2202/24* (2013.01); *G06T 2207/10048* (2013.01); *G06T 2207/30201* (2013.01)

(58) Field of Classification Search
CPC .... G02B 7/00; G02B 21/008; G02B 23/2415; G02B 27/0006; G05B 19/406; G05B 19/4155; G05B 2219/35111; G06F 3/041; G06K 9/00261; G06K 9/00288; G06K 9/00228; G06K 9/00268; G06K 9/00281; G06K 9/6202; G06K 2009/4666; G06K 9/00362; G06K 9/4642; G06K 9/6206; G06K 9/6255; G06K 9/6256; G06K 9/00275; G06K 9/00308; G06K 9/00926; G06K 9/3233; G06K 9/4671; G06K 9/6215; G06K 9/6228; G06K 9/6262; G06K 9/627

See application file for complete search history.

(56) References Cited

U.S. PATENT DOCUMENTS

| | | | |
|---|---|---|---|
| 2014/0336495 A1* | 11/2014 | Bittner | A61L 2/00 600/407 |
| 2015/0362603 A1 | 12/2015 | Ellwood et al. | |
| 2016/0168615 A1* | 6/2016 | Robbins | C12Q 1/04 435/5 |
| 2019/0357844 A1* | 11/2019 | Raupach | A61B 6/488 |
| 2020/0202148 A1* | 6/2020 | Wright | G06V 40/197 |

FOREIGN PATENT DOCUMENTS

| | | | |
|---|---|---|---|
| EP | 3461407 A1 | | 4/2019 |
| EP | 3646793 A2 | | 5/2020 |
| JP | 2022082320 A | * | 6/2022 |
| WO | WO-2020127883 A1 | * | 6/2020 |
| WO | 2023104558 A1 | | 6/2023 |

* cited by examiner

CLEANING SYSTEM OF A MEDICAL IMAGING FACILITY

FIELD OF THE DISCLOSURE

The disclosure relates to a computer-implemented method for the operation of a cleaning system of a medical imaging facility, wherein the imaging facility has an outer useful surface exposed to contaminating effects of patients and/or operators. In addition, the disclosure relates to an imaging facility, a computer program and an electronically readable data carrier.

BACKGROUND

In current clinical and out-of-hospital practice, for example in hospitals and/or radiology centers, a large number of different imaging modalities are in regular use, for example X-ray imaging, here in particular computed tomography imaging, and magnetic resonance imaging. Corresponding imaging facilities are usually relatively large systems, in a computed tomography facility, for example, formed by the gantry with the at least one receiving arrangement guided therein and a correspondingly moveable patient couch and in the magnetic resonance facility formed by the main magnetic unit containing the basic field magnets, which defines a patient receptacle into which the patient can likewise be moved by means of a patient couch. A very broad field of application is given for imaging radiological systems of this kind, and this extends from screening predominantly healthy people through to the examination of seriously ill patients. The diversity of these applications demands appropriate and targeted cleaning and disinfection of the imaging facility in order to prevent a transfer of infections and the like. In a pandemic situation in particular, disinfection of the imaging facilities, for example after the examination of a suspected case, becomes particularly important. This also applies to patients that are at risk for whom an infection can have particularly serious consequences.

One particular difficulty in the disinfection of imaging systems lies in the appropriate level of disinfection and cleaning. Very high hygiene requirements apply in the case of imaging facilities, which are situated for example in an operating theatre with direct patient contact during an intervention. However, the disinfection procedure in the case of imaging facilities in which the risk of infection is considerably lower is much more difficult. Specific examples of application of this are, for example, an X-ray facility in a radiology department in which a large number of patients, for example with broken bones or comparable internal injuries, are examined during the course of the day. Here the risk of infection is significantly lower and the assessment of the expenditure of time and material for appropriate disinfection of the imaging facility is considerably more difficult.

The task of the person responsible for hygiene or a hygiene specialist in situ is to define the preparation (cleaning and/or disinfection) for a medical imaging facility, for example to draw up a hygiene plan, and to ensure its implementation. On the basis of hygiene standards, such as the standard ISO 17664:2017, the manufacturer of critical, semi-critical and non-critical medical products and medical devices having direct contact with a patient are responsible for describing a validation of the preparation step in the usage instructions for the product/device. The manufacturer has only a limited direct influence on the content and implementation of the hygiene plan in order to reduce the potential dangers or dangerous situations, however.

From hygienic aspects the presence of a risk of infection is deemed a potential danger, which can affect patients, medical users and third parties. A dangerous situation results when contact is made with a surface. The more frequently contact occurs in the presence of active pathogens (danger), the higher the probability of the occurrence of infections can be.

Various normative fundamentals, for example the recommendation of the Commission for Hospital Hygiene and Infection Prevention (KRINKO) at the Robert Koch Institut (RKI) on the topic of surface disinfection, use the described underlying correlation for the classification of hygienically relevant surfaces (or ones for cleaning and possibly for disinfecting). It should be assumed in this connection that people who are at greater risk are found in an operating theatre or in an intensive treatment unit than, for example, in waiting rooms.

The previously customary procedure with imaging facilities has consisted in cleaning and disinfecting surfaces, in particular an entire useful surface, which can come into contact with patients and/or operators, in accordance with a specification, for example the hygiene plan.

Narrow patient receptacles always constitute a particular case, for example in the case of magnetic resonance facilities in which there is a relatively small diameter so there is only a short distance between the wall of the patient receptacle and the face of the patient. This can also result in the contamination of surfaces with aerosols if the patient sneezes or coughs, in particular also when he is merely breathing. This frequently results in the entire patient receptacle also having to be cleaned, and this can be extremely expensive and complicated in view of the length and the small diameter.

Furthermore, in a hygiene plan, which relates to the cleaning and disinfection of imaging facilities, frequently the entire room also has to be included, is possibly even cleaned since the cleaning and disinfection requirement is unclear. No feedback about the cleaning procedure takes place, moreover; the time expenditure and the further outlay are high and independent of an actual requirement. In addition, there is no way of verifying the cleaning which has taken place either.

SUMMARY

The disclosure is thus based on the object of disclosing a possibility for cleaning and disinfection of imaging facilities in the medical field, which is improved by comparison, in particular a cleaning quality associated with lower effort and which is improved and possibly also allows verifiability.

A method of the type mentioned in the introduction inventively comprises the steps therefore that during a utilization phase, in particular for an examination procedure of a patient, sensor data of a sensor arrangement detecting at least some of the useful surface is acquired and by evaluation of the sensor data a surface map having potentially contaminated regions of the useful surface is determined, and during a cleaning phase following the utilization phase, at least the contaminated regions are output to a cleaner as part of cleaning information and/or are used for actuation of at least one cleaning apparatus of the imaging facility for targeted cleaning of the contaminated regions.

The subject matter of the present disclosure enables, therefore an improved workflow in the preparation of medical imaging facilities after a utilization phase, in particular a use phase based on the examination of a particular, in other words a single, patient, so, for example, cleaning can take place after every patient or it is at least possible to assess whether cleaning and disinfection is necessary in preparation for the next patient. The term of the examination procedure or the utilization phase can also comprise interaction of an operator with the imaging facility that has taken place before and/or after the presence of the patient. Inventively, it is specifically proposed that contacted or generally potentially contaminated regions of a useful surface of the imaging facility exposed to potential contamination are detected with the aid of a sensor/lens system and are aggregated over time, specifically over the utilization phase. The sensors of the sensor arrangement in their entirety preferably defect the entire useful surface. Preferably, it is, as described, when the utilization phase comprises the duration of an examination procedure of an individual patient and the duration of the associated interaction with the imaging facility by an operator. For the cleaning phase, a cleaning operating mode can be activated, and this preferably takes place automatically after the end of the utilization phase, but is also manually conceivable, so it is in particular also possible that a user, in particular the at least one operator, ends the utilization phase and begins the cleaning phase. This will be illustrated in more detail below. In the cleaning phase, the detected and aggregated, contaminated regions of the useful surface, possibly together with additional information, for example cleaning instructions, are used as cleaning information to be displayed in order to thus make it clear to a cleaner where cleaning/disinfection is required, and/or, if provided, even cleaning apparatuses of the imaging facility can be actuated automatically for targeted cleaning of the contaminated regions. Cleaning apparatuses of this kind can be, for example, a UV irradiation facility and/or distribution apparatuses for disinfectant and/or a cleaning robot.

The detection of potentially contaminated regions (hereinafter called "contaminated regions" for short) by way of sensors makes it clear where a cleaning and/or disinfection requirement specifically exists, so the preparation can be directed to the actual requirement, whereby an unnecessarily high outlay in terms of time, finance and/or effort can be avoided. In other words, an optimized cleaning process adjusted to the actual requirement is enabled in the cleaning phase. Excessively time-consuming overall cleaning of the imaging facility, including its accessories such as local coils, support cushions and the like, as well as possibly the room in which the imaging facility is situated, can likewise be avoided if it is not required.

Owing to the increasing importance of hygiene demands in hospitals and similar establishments, the subject matter of the present disclosure offers a simpler possibility for the implementation of relatively high cleaning standards. The solution proposed here allows "Smarter Cleaning" due to its more targeted cleaning procedures, which, in particular, can be carried out faster. Careful cleaning of affected contaminated regions, instead of superficial overall cleaning, is made possible. The stress level for operators and cleaners, which results due to the need for cleaning, is reduced. Furthermore, the subject matter of the present disclosure also allows the risk to patients of being exposed to contact with pathogens on the imaging facility to be reduced.

Specifically, the imaging facility can be an X-ray facility, in particular a computed tomography facility, or a magnetic resonance facility and/or a housing unit with a patient receptacle into which the patient can be moved by means of a patient couch and/or can be brought by movement of the housing unit, with at least some of the surface of the housing unit and/or the patient couch being used as the useful surface. Whereas with a computed tomography facility the housing unit is conventionally referred to as a gantry, with a magnetic resonance facility it can be referred to, for example, as a main magnetic unit since, for example, the superconducting basic field magnet can be arranged in it. Imaging facilities constructed in this way have, in particular in the form of the inner wall of the patient receptacle, parts of the useful surface that are difficult to access and complex to clean, so accurate knowledge of where needs cleaning is extremely helpful and is also supplied within the scope of the present disclosure. The relative movement of patient and housing unit can take place by means of the patient couch; systems are also known, however, in which the housing unit is moved, for example in the case of interventional magnetic resonance facilities in which the housing unit can be mounted by means of rails on the ceiling.

The utilization phase can specifically be defined in such a way that after each examination procedure of a particular patient, a single patient therefore, and/or a predefined time interval, a cleaning phase follows and/or that a cleaning phase is triggered with a contamination satisfying a cleaning criterion indicated by the surface map. In addition, manual triggering of a cleaning phase is also conceivable. Preferably, it is alternatively after a fixed period, however, when the imaging facility or the cleaning system is automatically put into a cleaning operating mode, for example after each patient. However, it is also possible to begin a cleaning phase when a particular degree of contamination exists, a cleaning criterion is satisfied, therefore. A cleaning criterion of this kind can of course also obtain further information, for example state of health information relating to the patient, which can indicate, for example, that a patient is infectious, whereupon, for example, basically a cleaning phase can follow.

For evaluation of the sensor data it is generally conceivable within the scope of the present disclosure that at least partially at least one artificial intelligence evaluation algorithm, in particular comprising a neural network, is used. An artificial intelligence evaluation algorithm of this kind can also be referred to as a trained function. This is particularly preferred in view of image processing applications, in particular classification tasks.

In general, a trained function maps cognitive functions, which people associate with other human brains. By way of training based on training data (machine learning), the trained function is capable of adjusting to new conditions and detecting and extrapolating patterns.

Generally speaking, parameters of a trained function can be adjusted by training. In particular supervised learning, semi-supervised learning, unsupervised learning, reinforcement learning and/or active learning can be used. Furthermore, representation learning (also known as "feature learning") can be used. The parameters of the trained function can be adjusted, in particular iteratively, by a plurality of training steps.

A trained function can comprise, for example, a neural network, a Support Vector Machine, a decision tree and/or a Bayesian network and/or the trained function can be based on k-means clustering, Q-learning, kinetic algorithms and/or assignment rules. In particular, a neural network can be a deep neural network, a convolutional neural network (CNN) or a deep CNN. Furthermore, the neural network can be an adversarial network, a deep adversarial network and/or a generative adversarial network (GAN).

In a specific development of the present disclosure it can be provided that the sensor arrangement comprises at least one camera, in particular a 3D camera, and/or at least one microphone. Cameras, in particular 3D cameras and/or pairs of cameras positioned in such a way that three-dimensional information is to be determined, are particularly preferred, since with three-dimensional sensor data it is possible to assess much more efficiently whether, for example, contact is taking place and/or how close, for example, a part of a person comes to a region of the useful area. A microphone has proven to be useful, in particular, when aerosol contamination due to speaking, sneezing, coughing and the like is also to be tracked, since events of this kind can then be detected by corresponding detection of the associated noises. The use of at least partially optical cameras has the further advantage that people can be clearly identified, as distinguished from other objects/devices. Approaches to image processing, which can detect, for example, instances of contact since a person and/or a body part was classified as such, have already been proposed in the state of the art and can also be used in the present context.

At least one of the at least one cameras can particularly advantageously be a camera mounted on a ceiling of a room containing the imaging facility. Ceiling-mounted cameras can, for example, look down from above onto a work area, in particular a patient couch, with concealments of relevant parts by people occurring less often. With an imaging facility having a patient receptacle it can also be expedient to let at least one of the at least one cameras look into the patient receptacle laterally or rearwardly, for example outwardly from a wall. At least one of the at least one cameras can also be arranged on the imaging facility itself, at least for some imaging facilities. In addition, cameras that are present anyway for a different purpose can particularly advantageously also be used on and/or in the imaging facility and/or in a room containing the imaging facility within the scope of the inventive method in order to detect contaminated regions of the useful area and to be able to aggregate them in the surface map. Cameras of this kind can also serve, for example, for monitoring the patient for movements, for scanning the patient and/or for further functions. These are frequently already 3D cameras and/or sensors supplying three-dimensional information in some other way.

In particular, in addition to the at least one camera and/or the at least one microphone as parts of the sensor arrangement, of course further sensors and their sensor data can also be used, for example ultrasound sensors and the like. Furthermore, it is conceivable to provide the useful surface at least partially with contact and/or proximity sensors. For example, films have already been proposed in the state of the art, via which a contact and/or approach can be established, for example capacitively, extensively and nevertheless in a spatially resolved manner. A film of this kind and/or another sensor concept of this kind can be arranged, for example, in the form of a coating on the useful surface. Useful sensor data for the determination of the surface map also comprises sensor data from actuation sensors, which can be provided, for example, on operating elements of the imaging facility, which form part of the useful surface, in order to be able to detect operating measures at the operating elements. It is thus possible to understand, for example, which operating elements were used, and possibly also where.

For determination of at least part of the surface map during the utilization phase by way of an image processing algorithm, which evaluates the sensor data of the camera, instances of contact with the useful surface made by a current patient and/or a current operator and/or aerosol generating procedures relating to aerosol pollution of the surface, in particular respiration processes, can preferably be detected, with contacted regions of the useful surface and/or regions affected by aerosol generating procedures being marked as contaminated regions. For example, it is conceivable therefore to track people and/or their body parts, in particular exposed body parts, in particular the arms, hands and/or the head, by way of an image processing algorithm. Instances of contact with the useful surface by body parts can be established by means of the image processing algorithm and the corresponding contacted regions of the useful surface can be marked as contaminated regions in the surface map. In particular with tracking of the head of the patient it can specifically be provided that head tracking, in particular of the patient, is carried out for detection of respiration processes relating to aerosol pollution of the useful surface, with relevant aerosol pollution for the head positions being detected as a function of a distance of the head, in particular of the face, from the useful surface and/or a length of stay in the head position. In particular, the position of least one person, in particular of the patient, can be monitored throughout the examination procedure or the utilization phase therefore, and regions, which were situated too close and/or for too long in the area of influence of the face of the person can be marked as contaminated. This is useful and relevant in particular in imaging facilities, which have a patient receptacle, in particular a narrower one, in which the head of the patient, when it is in the patient receptacle, can be situated very close to the corresponding wall of the patient receptacle.

In an advantageous development of the subject matter of the disclosure it can also be provided that at least some of the sensor data of the camera is acquired by illumination of at least some of the useful surface with UV light, in particular black light and/or by means of a UV irradiation facility also used as a cleaning apparatus, with regions of the useful surface that glow under the illumination being detected in the evaluation of the sensor data at least partially as being contaminated. It has been found that a large number of bodily fluids, in particular also aerosols, can become particularly visible, in particular glowing, on useful surfaces under black light so contaminations of this kind can be identified particularly easily in the sensor data on illumination with an appropriate illumination facility (UV irradiation facility). An embodiment of this kind is useful, in particular, in connection with further evaluation processes of the sensor data, which can be based for example on coughing, sneezing, speaking and the like, or track the position of the head/face since then a reciprocal validation is possible. Reference should be made in this connection to the fact that a lighting facility of this kind can already be provided, for example as a cleaning apparatus, since UV light is known to kill particular pathogens. For example, UV light sources, in particular black light sources, can be provided inside a patient receptacle therefore and, apart from a use as a cleaning apparatus, are also used for improved detection of instances of contamination, in particular those which require further cleaning/disinfection.

While the use of customary cameras that operate in the range of visible light, in particular 3D cameras, is already useful, problems also occur in this regard, however. Firstly, there is the difficulty that a continuous line of sight between the camera and useful surface to be observed is necessary in order to be able to decide which regions of the useful surface were contacted by the operator/the patient and were potentially contaminated thereby. Furthermore, dripping fluids or similar can only be detected with extreme difficulty by a normal camera operating only the visible light range. It is thus conceivable, for example in the case of a patient, for blood, wound secretion, saliva, vomit, urine or any other fluid including medicine, infusion fluid or another fluid to unintentionally drip onto the useful surface.

A particularly advantageous development of the subject matter of the present disclosure provides therefore that at least one of the at least one cameras is an infrared camera, wherein instances of contact are detected on the basis of a temperature difference of a current image from at least one comparison image, acquired previously, in particular on completion of the last cleaning phase, containing temperature information. An infrared camera of this kind can also be referred to as a thermal image camera. It is proposed therefore that an infrared camera, mounted for example on the ceiling, is used for observation of the useful surface. A 3D camera can preferably also be used here as the infrared camera; it is also conceivable, however, that a second camera is used for detection of the depth information of the scene. A thermal image camera as part of the sensor arrangement enables detection of the regions of the useful surface contacted during the course of an examination. A more specific procedure for example can be provided in this case:

Detection of the initial condition of the useful surface with the aid of the infrared camera. This can take place in the form of said comparison image, which describes reference temperatures, in particular also a single reference temperature, if the useful surface has a temperature that is at least substantially constant, therefore.

In the beginning of the examination, the patient and the at least one operator, medical staff therefore, enter the room in which the imaging facility is arranged and change the detected temperature information. If, for example, an operator grasps the patient couch in order to prepare it for the patient, and lets go of it shortly thereafter, the patient couch is heated as part of the useful surface in the contacted region. This is mapped in current sensor data of the infrared camera, a thermal image or temperature image, therefore. The change in temperature can be determined by the formation of difference images of the infrared camera and thus the potentially contaminated regions can be marked in the surface map. Of course other sensor data or evaluation results of other sensor data can also be used by way of validation and/or supplementation.

As described, in the cleaning phase the cleaner can then be provided with the aggregated potentially contaminated surfaces as the cleaning information.

Compared to other 3D camera approaches, the use of a thermal image camera allows a considerable improvement in the detection of instances of surface contact. The central advantage can be seen in that contacted regions are heated and the elevated temperature is output over the time. A retrospective detection is thus possible as soon as a direct line of sight exists again between the infrared camera and the corresponding region on the useful surface.

In addition to the simplified possible tracking of occurrences of contact, it can also particularly advantageously be provided in this embodiment that, in addition to instances of contact, the presence of bodily fluids on the useful surface is also detected using the temperature difference, with regions of the useful surface having bodily fluids also being marked as contaminated. Bodily fluids as well as other fluids, which have a temperature differing from the surface temperature, in particular reference temperature, of the useful surface, can be detected via the infrared camera, specifically the sensor data thereof, and this provides further, useful information on a potential contamination. If during the analysis, for example of a difference image comprising the comparison image and a thermal image formed from the current sensor data of the infrared camera, a change in temperature can be established, for example by way of an image processing algorithm, in particular without a body part having previously spent time at this location, possibly also by taking into account the appearance and/or the temperature differences, it is possible to detect fluids, in particular bodily fluids, on the useful surface.

In a particularly advantageous development of the subject matter of the present disclosure, when an infrared camera is used it can be provided that a contact and/or contamination intensity is derived in order to determine a level of contamination from the value of the temperature difference. Detection of the temperature, or specifically the temperature difference, means that in addition it is particularly advantageously possible to estimate the intensity of the contact. Heating in the case of intensive skin/body contact thus has a tendency to be greater compared to contact with an item of clothing. Furthermore, greater heating occurs with longer contact. Information of this kind is much more difficult to detect with the aid of a conventional camera that operates with light visible to humans.

In a general development when a camera is used as part of the sensor arrangement it can be provided that without the presence of people and additional objects in the field of view of the at least one camera, in particular together with the comparison image, a geometry reference image is acquired, which describes the three-dimensional geometry, in particular comprising the three-dimensional course of the useful surface, with, in particular, people and/or objects obscuring the useful surface being detected by formation of difference images of the geometry reference image with at least one currently acquired image and being taken into account when determining contaminated regions. In particular, when an infrared camera is used, depth information can be added to the comparison image by way of such a geometry reference image, which information can be used again in this context. It should also be noted at this point that in order to determine the geometry of the useful surface, which is expedient in the assessment of instances of contact, proximity of heads and the like, other sources can of course also be used in addition or as an alternative, for example other sensors of the sensor arrangement, a model describing the geometry of the imaging facility, and thus also the useful surface and/or information on the current position of movable parts of the imaging facility.

In a further, particularly advantageous development of the subject matter of the present disclosure it can be provided that during the course of the sensor data evaluation, aerosol generating procedures are detected by way of an aerosol contamination algorithm by detection of speech and/or sneezing noises and/or coughing noises in the sensor data of the at least one microphone and/or of, in particular jerky, movements in the head region of a person detected by the at least one camera, in the sensor data of the at least one camera, with regions of the useful surface affected by a detected aerosol generating procedure being marked as contaminated. In the framework of this embodiment it was found that in particular with the existence of sensor data of a microphone or a plurality of microphones, procedures leading to aerosol contamination, namely aerosol generating procedures, can also be sufficiently reliably detected. While it is basically conceivable in this connection to classify, for example, noises by comparison with reference noises, in particular by pattern extraction, and to then define by way of conventional image processing algorithms suitable, in particular jerky, movements of the head of people detected in the camera image, a particularly advantageous embodiment of the present disclosure provides that the aerosol contamination algorithm comprises an artificial intelligence trained function, with the trained function being applied to input data comprising sensor data of the microphone and/or the camera to obtain output data describing the presence of at least one aerosol generating procedure. Examinations in this connection have shown that artificial intelligence and machine learning may be applied particularly advantageously and effectively in order to detect such aerosol generating procedures, in particular for occurrences of sneezing and/or coughing. Audio and video signals, sensor data of the at least one microphone and the at least one camera therefore, possibly in addition to further input data, are fed to the trained function of the aerosol contamination algorithm, which then identifies sneezing and coughing and possibly further aerosol generating procedures, in particular on the part of the patient, which is characterized by jerky body movements combined with the corresponding noises. It should also be noted at this point that microphones on or in the imaging facility can also serve further functions, for example communication with the patient.

For example, sensor data of at least one further sensor of the sensor arrangement and/or at least one evaluation result of sensor data of the sensor arrangement, in particular in respect of an illumination with UV light, and/or state of health information describing the state of health of the patient can be used as further input data the trained function. As already described, the UV light can particularly preferably be black light. For example, locations at which bodily fluids, in particular also aerosols, are present on the useful surface, can be identified by black light, and these locations can be compared by way of the aerosol contamination algorithm with the sites at which, according to the evaluation of the sensor data of the camera and of the microphone, contamination is expected owing to detection of aerosol generating procedure. In particular, the trained function can be designed to both identify by way of UV light, in particular black light, contaminations due to bodily fluids as well as detect aerosol generating procedures, so both types of information can be merged to mark contaminated regions of the useful surface in the surface map.

State of health information about the patient, which describes their health status, can be taken into account by the trained function. State of health information of this kind can be retrieved for example from an electronic patient file, a Radiology Information System (RIS), a patient registration or the like. It is also conceivable, however, to infer this from an input by an operator, which has identified, for example, that the patient is not well or has obtained this information from the patient.

It should also be pointed out that—independent of the use of an aerosol contamination algorithm—state of health information of this kind can also generally be determined and output at the beginning of the utilization phase and/or the cleaning phase. In this way, an operator and/or a cleaner can adequately take account of the state of health information. If, for example, an operator knows in advance that a highly infectious patient is to be examined, the operator can employ prevention measures to reduce contamination as early as in the utilization phase. A cleaner can conclude that there is a particularly high risk and similarly use this as a reason to carry out particularly thorough cleaning. Finally, it is also generally conceivable, however, to use state of health information of the patient generally in the evaluation of the sensor data, for example to increase a general risk level, which can reduce for example thresholds above which a contamination is identified, and the like. Such thresholds can relate, for example, to the distance of the head of the patient, in particular of the face, from regions of the useful surface, but also contact times or the like, as far as the useful surface is concerned.

In respect of the aerosol contamination algorithm, other input data, beyond said examples, can of course also be used to obtain an optimum evaluation of the sensor data in view of aerosol generating procedures. If, for example, further information is available in addition of the patient status information, for example jointly stored in the source thereof, or if additional sensors are present, their sensor data can similarly be evaluated by the aerosol contamination algorithm, in particular the trained function, and thus improve the evaluation results.

The output data can particularly advantageously also comprise a classification of the aerosol generating procedure and/or the region contaminated by the aerosol generating procedure and/or information comprising the severity of the contamination, in particular a level of contamination. If, therefore, the trained function establishes am aerosol generating procedure, for example sneezing or coughing, it is also possible to determine the current position of the head of the person, in particular of the patient, and in which direction the face is angled. Accordingly, an affected portion of the useful surface results as a potentially contaminated region, in particular also from the severity of the aerosol generating procedure. In particular it is also possible to identify the severity of the contamination and to also output it, preferably as a level of contamination. Thus for example aerosol/bodily fluid can be hurled quickly and widely by extreme bouts of coughing and/or sneezing, so a more severe contamination of the potentially contaminated region can be assumed than, for example, with straightforward speaking and/or breathing.

In particular when, and this will be discussed in more detail below, a plurality of evaluation approaches are selected, for example when the procedure is additionally based on differences in temperature when an infrared camera is used, it is expedient if all these partial evaluations provide levels of contamination, which can be assigned to the potentially contaminated regions in the surface map. If potentially contaminated regions owing to the same cause or owing to different causes have been determined by a plurality of partial evaluations, the corresponding levels of contamination can be merged, for example by a mean or, in the case of a plurality of causes, also additively, and by way of similar calculations.

The trained function can be, in particular, a neural network, in particular a convolutional neural network (CNN). To provide the trained function it, for example the neural network, can be trained with training data. Training input data, comprising sensor data of a camera and/or a microphone, with assigned training output data, which describes an expected result, can be used for training the trained function. In other words, by way of example video and audio recordings of people who are coughing, sneezing, talking or are even quiet, can be used. An expected result is defined for each of these training data sets. The function, in particular the neural network, is trained on the basis of this training data that has been supplemented in this way.

During the run time, in other words the evaluation of sensor data in the utilization phase, audio and video signals are fed as sensor data of the camera and the microphone to the trained function, possibly with further input data, and thus stored in the neural network. The network particularly advantageously then also calculates a level of contamination, for example 25%—slight contamination due to talking, through to 100%—severe contamination due to heavy coughing, as output data. In view of such a level of contamination also, the training data sets can be adjusted in the form of the defined result, so appropriate training takes place. Of course training input data also includes, if, in addition to the sensor data of the at least one camera and the at least one microphone, even further input data is to be used, this further input data, for example information on the illumination under UV light and the like.

As already mentioned, in the present disclosure it can also generally be expedient if a level of contamination describing the severity of the contamination is determined in the evaluation of the sensor data, which level is taken into account in the selection of the contaminated regions to be output and/or is output with the contaminated regions and/or is used for the selection of treatment information to be output with the contaminated regions. Such a level of contamination and its determination were already addressed in respect of the infrared camera and in respect of the aerosol contamination algorithm, where it can be deduced, for example, from the severity of the aerosol generating procedure. Of course, generally a level of contamination can also be determined, for example from the duration of a contact, the fact whether contact occurred by way of an item of clothing or directly, the type of contact and the like. A level of contamination can be beneficially used in many ways. For example, it can form a threshold, so, for example, regions that are only very slightly contaminated do not necessarily have to be output for each cleaning phase. Furthermore, it can be output for further information for a cleaner together with the respective contaminated regions, however, so for example a cleaner can identify where particular effort is required and where the normal cleaning procedure can be sufficient. In other words, a level of contamination allows thorough cleaning/disinfection of potentially contaminated regions to be provided, in particular in the case of severe contamination, instead of superficial overall cleaning or uniform cleaning of all contaminated regions that is not sufficiently effective. In other words, smarter cleaning is achieved.

This can be additionally or else alternatively supported by selecting treatment information to be output with the contaminated regions on the basis of the level of contamination. Treatment information of this kind, which can also be referred to as a cleaning instruction, can include, for example, a cleaning tool to be used, a cleaning agent to be used, a cleaning time and the like and thereby constitutes an additional item of information, which can be included in the cleaning information in addition to the surface map or the potentially contaminated region. This kind of treatment information makes it particularly easy to approach the level of contamination appropriately. It should be pointed out that a contamination category on the basis of the evaluation result can also be assigned to potentially contaminated regions, moreover, preferably in addition to the level of contamination, so for example with contamination due to bodily fluids/aerosols of an aerosol generating procedure, a different type of cleaning can be used than with contamination that has come about due to instances of contact.

The sensor arrangement can expediently also comprise at least one temperature sensor from whose sensor data a body temperature of the patient is derived, which is used in the classification as a contaminated region and/or when determining a or the level of contamination. While the temperature sensor is basically conceivable as a particular use of the infrared camera, it is only expedient, however, if it is designed for the determination and assignment of absolute temperatures. Dedicated temperature sensors are also conceivable, however, which can be placed in particular at sites which come close to the patient, for example inside the patient receptacle. Such temperature sensors can then determine information about the body temperature of the patient, and this can be used for example when determining state of health information and/or can also be directly incorporated in the contamination estimate. If, for example, fever is established in the patient, it can be assumed that they are carrying an infectious disease, so for example threshold or limit values, above which a region is marked as being contaminated, can be adjusted, as has already also been described in respect of the state of health information. Even when a level of contamination is determined, a body temperature of the patient constitutes a useful input variable. Generally, it can be said that as the body temperature of the patient increases, a generally higher risk of infection, and thus a greater criticality of contaminations, is assumed.

If the imaging facility has at least one movable component, a particularly advantageous embodiment of the present disclosure provides that at the beginning of the cleaning phase the at least one movable component is moved into a specified cleaning position. This means a predefined state of cleanliness of the imaging facility can exist in which, for example, the useful surface, viewed across all of its portions, can best be reached/cleaned. For example, whenever the system is put into a cleaning operating mode at the beginning of the cleaning phase, a dedicated cleaning position can be assumed for each movable component, for example the patient couch, therefore. It is also conceivable, moreover, to define a plurality of such specified cleaning positions, in particular at least two states of cleanliness of the imaging facility, so for example for different sub-phases of the cleaning phase, different cleaning positions can be provided for at least some of the movable components, which in each case offers optimum access for the corresponding sub-phase or the contaminated regions in them that are to be cleaned and disinfected.

A particularly advantageous development of the subject matter of the present disclosure provides that at least one additional item of information, in particular a cleaning protocol and/or dependent on the instant of the beginning of the cleaning phase, is added to the cleaning information, in particular at the beginning of the cleaning phase. Additional information of this kind can comprise, for example, additional regions of the useful surface and/or other surfaces that have to be compulsorily cleaned, and/or the cleaning extent of regular cleaning and/or cleaning to be carried out owing to a specific circumstance, in particular end-of-day cleaning and/or weekend cleaning and/or deep cleaning. The additional information is particularly preferably likewise output to the cleaner as part of the cleaning information.

In other words this means that, for example, cleaning protocols can be merged with the surface map, the detected contamination information therefore, in order for example to satisfy both the cleaning protocol, for example a hygiene plan, and to clean the regions of the useful surface specifically detected as being contaminated. If it is provided, for example, that particular regions/surfaces are to be compulsorily cleaned in the case of end-of-day cleaning or weekend cleaning, this can ultimately be added to the cleaning information, wherein the additional information can of course also comprise treatment information for such regions that should additionally be cleaned, which can possibly, if contaminated regions of the surface map and regions that are to be compulsorily cleaned match in accordance with a cleaning protocol, take precedence over the more thorough cleaning method. In other words, this means that even, for example, in the case of deep cleaning or weekend cleaning, the cleaning information can direct the attention of the cleaner to particular regions contaminated in the last utilization phase and these can be subjected to sufficiently thorough cleaning and disinfection.

The additional information, in particular the cleaning protocol, can particularly advantageously be created and/or adjusted on the basis of a user input, in particular at the imaging facility and/or at a central administrative facility. This means cleaning protocols, for example, can be centrally or decentrally personalized, administered and created by a user, for example a person responsible for hygiene. In particular in this connection, instants and/or periods can also be added to the additional information, in particular cleaning protocols, in which they are to be applied, in particular in the case of end-of-day cleaning and/or weekend cleaning. The use of additional information, in particular cleaning protocols, can serve, for example, for quality assurance in respect of medical care.

In a particularly preferred embodiment of the disclosure it can be provided that the contaminated regions and/or further regions of the useful surface included in the cleaning information as regions to be cleaned, can be visualized in a space-resolved manner by means of a display facility. In this way, a cleaning requirement at the location of the useful surface can be visualized where it exists, so a particularly intuitive communication to the at least one cleaner is possible and it is also ensured in an improved manner that cleaning takes place after it can be accurately identified where cleaning should occur and whether the contaminated region has already been dealt with completely.

In a particularly advantageous development of the subject matter of the present disclosure it can be provided that at least one projection facility and/or a display layer provided on and/or below the surface, in particular an OLED layer, is used as the display facility. These types of display facility have the advantage that they can display contaminated regions on the useful surface in a space-resolved manner in that, for example, appropriate cleaning information is projected onto the contaminated region and/or the display layer is locally actuated in the contaminated region. For this purpose, the at least one display facility is of course registered with the sensor arrangement and thus the surface map. Projection facilities as display facilities can be mounted, for example, at positions at which cameras and/or other sensors are also provided, for example on a ceiling of a room containing the imaging facility. With projection facilities an arrangement on the imaging facility itself can also be provided, for example inside a patient receptacle. As far as display layers are concerned, they can be combined, for example together with a contact and/or proximity sensor system integrated in the useful surface, for example in the manner of a touchscreen. In particular when OLED films are used or related display layers, dedicated information, for example a level of contamination, can also be presented since then the portions of the useful surface provided with the display layer ultimately form an overall display surface.

The space-resolved display when determining a level of contamination can particularly advantageously be configured to display the level of contamination and/or the treatment information. In other words, it is possible to show the cleaner not only which contaminated regions must be cleaned but also how severely contaminated they are and how intense the cleaning must be, therefore. For example, a color marking of yellow for a less severe contamination through to dark red tones for severe contamination is conceivable here. In other words, different levels of contamination can be differentiated in the form of visually distinguishable presentation.

In addition, the treatment information already mentioned and/or additional information can of course also be at least partially integrated in the space-resolved visualization. For example, cleaning instructions, for example permitted cleaning agents, methods or required work steps, can be presented therefore, preferably as a function of the imaging facility at hand, for example by an alternative accentuation/presentation of contaminated regions and the like.

In an expedient embodiment of the present disclosure it can also be provided that if state of health information describing the state of health of the patient to be examined next in the imaging facility is received at the beginning of the cleaning phase, in the case of state of health information describing a greater sensitivity of this patient to infections (referred to as a high-risk patient), the surface map and/or the cleaning information is adjusted to achieve a greater, better therefore, level of cleaning. If particular health problems/risks are known therefore in the case of the next patient to be examined, which make him or her more sensitive to infections, the cleaning system can automatically increase the risk level, for example, to ensure that the imaging facility is cleaned intensively and attentively before the examination procedure begins for this patient.

In an expedient development of the method it can be provided that the cleaning information is output at least partially acoustically and/or haptically and/or by means of a presentation facility provided in particular in addition to the display facility. Appropriate output means can be provided for the acoustic and/or haptic output. In particular when it is not possible to completely present the cleaning information, in particular the treatment information and/or the additional information, in a space-resolved manner by means of the display facility, it is also conceivable to output it for example in a display suitable for this purpose, generally a presentation facility such as a monitor, a touchscreen or the like. In other words, in addition or as an alternative to display facilities designed for space-resolved display of contaminated regions or other cleaning information, other optical output means (presentation facilities) are also conceivable, for example monitors/screens mounted on the imaging facility on which the cleaning information can be at least partially presented, in particular also as far as the treatment information and/or additional information is concerned. Of course display facilities that are provided on the imaging facility anyway can also continue to be used, for example also for the operation of virtual touchscreens at an end face of a gantry/main magnetic unit, a monitor arrangement comprising at least one monitor for the display of acquired image data and the like.

Cleaning instructions and/or other additional and/or treatment information can also be described acoustically by a corresponding output means, while haptic feedback to the cleaner is also conceivable. As already mentioned, the cleaning information can also be provided at least partially in electronic form for automatic evaluation of the instructions, for example for actuation of a cleaning robot and/or a cleaning apparatus installed in the imaging facility. It is not just monitors, screens, touchscreens and the like, which can be provided in particular on the imaging facility and which are suitable as presentation facilities, moreover: it is also possible that the presentation facility is a projection facility, which can be designed, for example, to project at least some of the cleaning information onto a suitable surface, for example a wall surface of the room containing the imaging facility.

In a preferred embodiment, by taking into account the surface map, in particular with additional use of the additional information and/or the level of contamination, it can also be provided that a workflow describing, in particular, the order and/or cleaning direction of contaminated regions to be cleaned is determined and output. Such a cleaning workflow can also be output in a space-resolved manner by a display facility, for example by the serial numbering of connected contaminated regions; alternatively or in addition also on a presentation facility. The order of the space-resolved presentation of the contaminated regions can also be geared to such an order determined for optimization of the cleaning process. A cleaning direction, for example a wiping direction, of contaminated regions to be cleaned can be output, for example in the form of projected arrows and/or arrows displayed in a space-resolved manner in some other way. In this way, by taking into account particular criteria, which can take into account, for example, an interaction of contaminated regions and/or effects of the cleaning methods, it is possible to determine optimum cleaning workflows that provide for an outstanding cleaning performance, it being possible to deal with, for example, regions contaminated by bodily fluids, where there is also the worry about dripping onto other regions, earlier and with a subsequent substitution of the cleaning fluid and the like. In a different determination rule for a cleaning workflow, starting, for example, from the patient receptacle to portions located ever further out, this can be progressed, for example, to the remote end of the patient couch.

In an expedient development of the subject matter of the disclosure it can be provided that the cleaning information is output at least partially using an augmented reality facility, in particular augmented reality glasses. Augmented reality (AR) can particularly advantageously also be used within the scope of the present disclosure, with an augmented reality facility ultimately superimposing additional information, here the cleaning information, on the reality. This can occur particularly advantageously using augmented reality glasses with a projection surface onto which the cleaning information can be projected. A contact-analogous presentation is also conceivable in the case of such an augmented reality facility, which means the cleaning information, for example the presentation of a contaminated region from the surface map, is presented to a user exactly superimposed on the corresponding real portion of the useful surface.

In a particularly preferred embodiment of the present disclosure, the sensor arrangement can also be operated during the cleaning phase for acquisition of sensor data, which is evaluated for determination of monitoring information describing the performance and/or result of cleaning measures. In other words, the interaction of the cleaner with the imaging facility, in particular the useful surface therefore, can be detected for the preparation thereof, for which purpose the sensor arrangement, in particular a 3D camera, can again be used. It can be provided, for example, that processing and/or results information in respect of this cleaning is determined as the monitoring information for each contaminated region, with the output of the contaminated region being changed in order to display its processing and/or effective cleaning. In this way, a cleaner can identify as early as when they carry out cleaning the result of their cleaning and also assess the work remaining. Direct feedback can thus be generated using the sensor arrangement, and this can also be used to give instructions for as yet incomplete cleaning of a contaminated region, so cleaning can be guaranteed in an enhanced manner. For example, the color can change with space-resolved presentation in order to display effective cleaning/processing of a contaminated region, with fading out also being conceivable. With a space-resolved display, the contaminated region can be wiped, for example by the cleaning procedure, as it were from its previous color indicating contamination, for example a red tone, to a green tone.

It is also expedient in this connection if completion information indicating the completion of all cleaning measures is determined as the monitoring information, and this is likewise output, in particular at the completion of the cleaning phase and/or at the beginning of the next utilization phase. Ultimately, evidence of cleaning that has taken place is generated in this way. Successful implementation of preparation of the imaging facility, of the cleaning process therefore, can be suitably presented and documented. For example, the completion information can be made transparent for the next patient, so patient satisfaction is increased. For the cleaner this procedure achieves an increased level of confidence in their own work and a confirmation of the result of their work. Specifically, it is conceivable, for example, to illuminate the entire useful surface in green or the like with a space-resolved presentation.

Expediently, the cleaning information and/or the monitoring information and/or the completion information can be archived for the purpose of logging and/or for subsequent evaluation. While analog logging is basically conceivable, digital logging is preferable, it being possible for the operator and/or manufacturer of the imaging facility to be provided with the information. In this context it can particularly advantageously be provided that the archived information is statistically evaluated, in particular with regard to an embodiment of imaging facilities that is improved in respect of the contamination and/or cleaning and/or for the improvement of cleaning measures and/or improvement of the cleaning system and/or with regard to predictive maintenance. A statistical acquisition and evaluation of the performance of the cleaning process/of the detection procedure is given thereby, which can be used, for example, for the optimization of future products or also for predictive maintenance. An optimization of the system interaction for operators and the like is also possible.

Apart from the method, the present disclosure also relates to an imaging facility, having a cleaning system with a sensor arrangement and a control facility designed for carrying out the inventive method. All statements in respect of the inventive method may be analogously transferred to the inventive imaging facility with which the advantages already mentioned can likewise be obtained, therefore.

Within the context of integration of the cleaning system in the imaging facility, the control facility of the imaging facility can also be the control facility of the cleaning system. This is especially expedient when sensor data of the sensor arrangement is to be evaluated not only in view of the detection of potentially contaminated areas of the useful surface but also for functions of the imaging facility itself, for example with regard to patient monitoring and/or patient scanning and/or patient communication.

The control facility can include at least one processor and at least one storage means, the same as at least one function unit in order to be able to carry out corresponding steps of the inventive method. For example, the control facility can have an evaluation unit for evaluation of the sensor data and for determination of the surface map. The cleaning information can be compiled in a preparation unit and be output by actuation of the corresponding output means, for example the display facility and/or the presentation facility and/or acoustic and/or haptic output means, which can also be understood as pertaining to the cleaning system. Further function units for the implementation of further method steps are of course also conceivable in specific exemplary embodiments.

An inventive computer program can be loaded, for example, directly into a storage means of a control facility of a cleaning system and has program means in order to carry out the steps of an inventive method when the computer program is run in the control facility of the cleaning system. The computer program can be stored on an inventive electronically readable data carrier, which comprises electronically readable control information stored thereon therefore, which comprises at least one said computer program and is configured in such a way that it carries out an inventive method when the data carrier is used in a control facility of a cleaning system. The data carrier can be a non-transient data carrier, for example a CD-ROM.

It should be noted that within the scope of the present disclosure it is basically also conceivable to provide the cleaning system as a separate product. The cleaning system then comprises the sensor arrangement, the control facility designed for carrying out the inventive method, and output means and should be installed in the surroundings and/or on/or in the imaging facility, for example within the context of a retrofit/extension. Generally, the cleaning system can also be referred to as a hygiene system, moreover.

BRIEF DESCRIPTION OF THE DRAWINGS

Further advantages and details of the subject matter of the present disclosure can be found in the exemplary embodiments described below and with reference to the drawings, in which.

DETAILED DESCRIPTION

Figure 1:
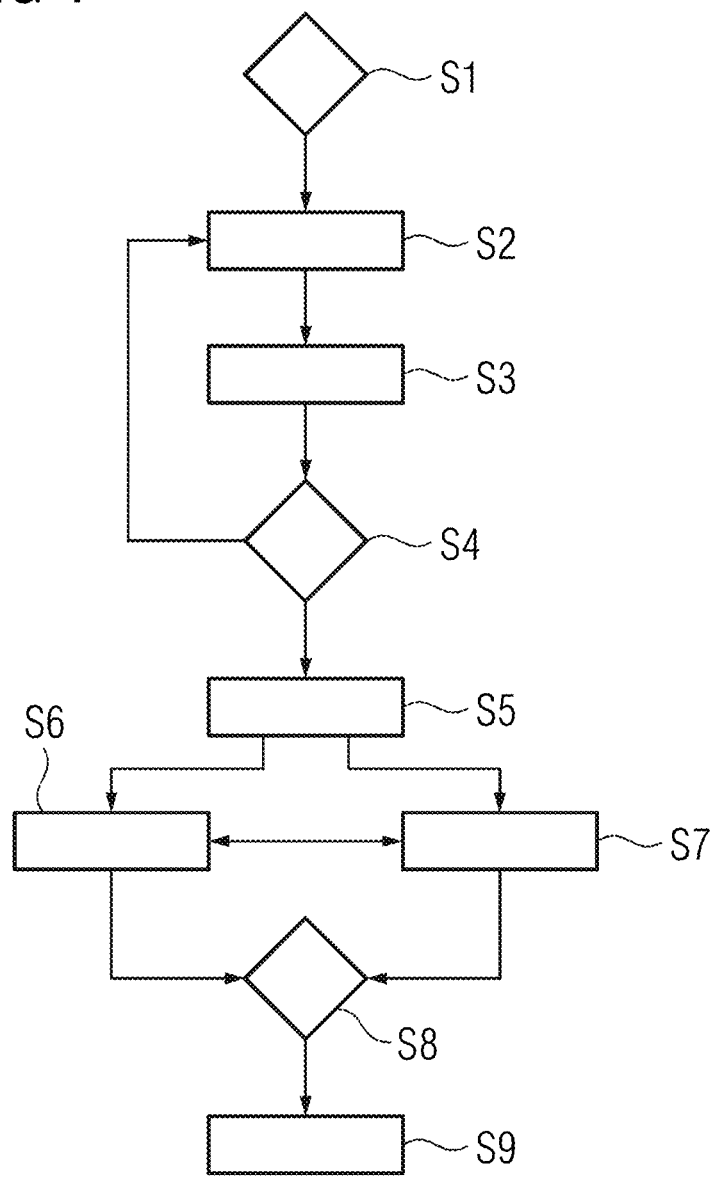
FIG. 1 shows a flowchart of an exemplary embodiment of the inventive method.

FIG. 1 shows a flowchart of an exemplary embodiment of the inventive method. This is used during operation of an imaging facility, during its use for the examination of patients, therefore. In addition, the imaging facility has a cleaning system, which tracks potential instances of contamination/soiling and is used in a cleaning phase, which follows a utilization phase beginning in step S1 in FIG. 1, to assist the at least one cleaner.

Figure 2:
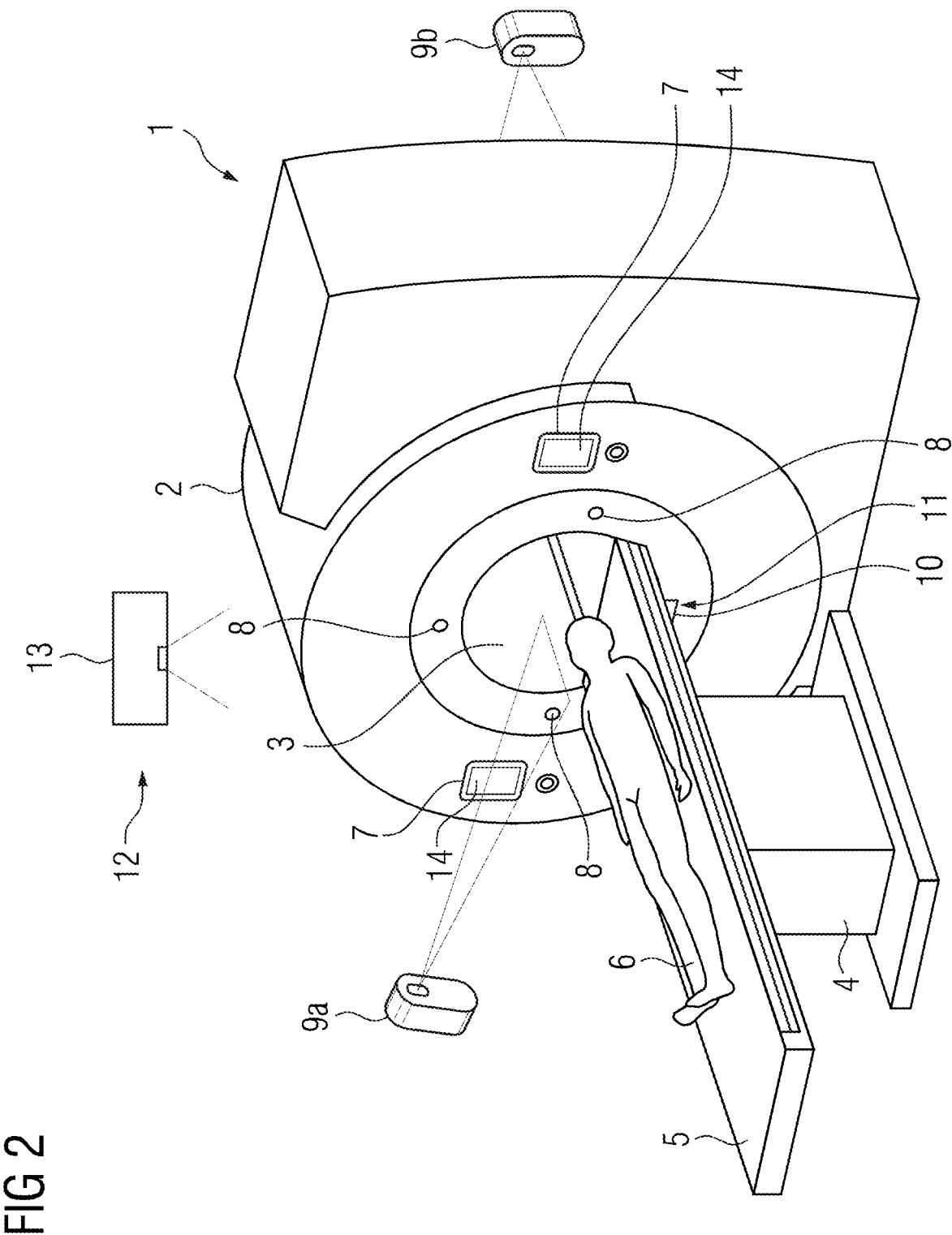
FIG. 2 shows a view of an inventive imaging facility.
Figure 3:
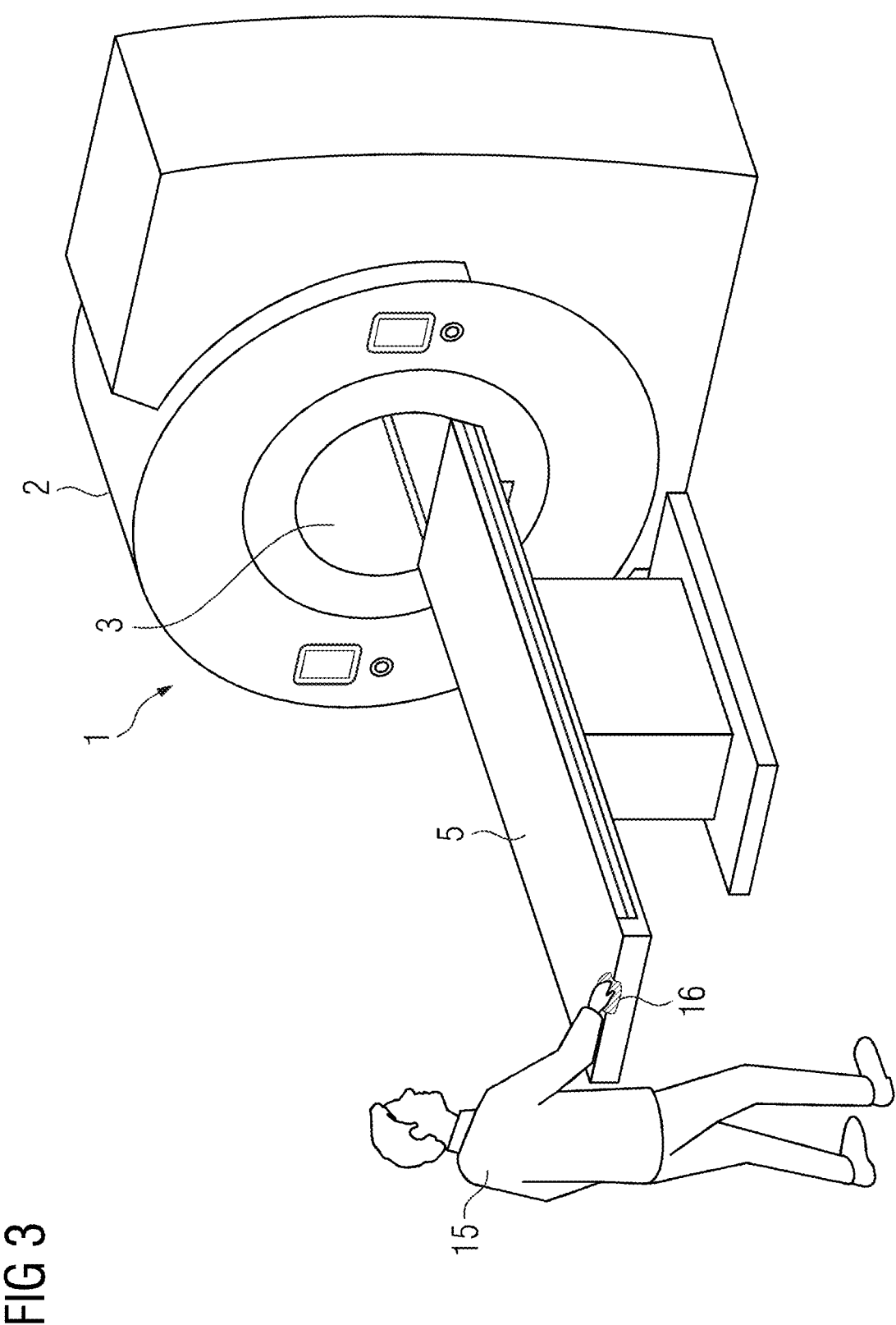
FIG. 3 shows a first situation during a utilization phase.

The exemplary embodiment is to be explained by means of an inventive imaging facility 1, as presented in FIG. 2.

The imaging facility 1 is, by way of example, a magnetic resonance facility in which a housing unit 2, which defines a cylindrical patient receptacle 3, can also be referred to as a main magnetic unit since it contains the basic field magnet. For example a radio frequency coil arrangement and a gradient coil arrangement (not shown) can be provided so as to surround the patient receptacle 3. Apart from the housing unit 2, the imaging facility also comprises a patient table 4 with a patient couch 5 supported thereon, on which a patient 6 can be supported and be moved into the interior of the patient receptacle 3. In the present case, operator facilities 7 comprising a touchscreen as the operating element are provided for the operator on other side next to the patient receptacle 3.

In the present example, the imaging facility 1 accordingly also has a cleaning system, which, apart from a control facility (not shown here) and output means, comprises a sensor arrangement, of which three microphones 8 and two cameras 9a, 9b are show by way of example in FIG. 2. For example, the camera 9a can be arranged on the ceiling of a room containing the imaging facility 1, while the camera 9b is arranged on a wall of the room in such a way that it is possible to look into the patient receptacle 3. A black light facility 10, which can support both the acquisition of sensor data relating to contamination by way of the cameras 9a and 9b but secondly also acts as a cleaning apparatus 11 since it irradiates UV light, which can also kill at least some potential pathogens, is also indicated as a UV irradiation facility, moreover. Further sensors of the sensor arrangement can be formed by actuation sensors of the operating elements of the operator facilities 7. In addition or in alternative exemplary embodiments, the useful surface can also be provided at least partially with a film providing proximity sensors and/or contact sensors.

One projection facility 13 is shown purely by way of example as an output means 12, and this can also be mounted on the ceiling; expediently, a plurality of projection facilities 13 is provided, so an entire, pre-defined useful surface is covered by the respective projection surfaces. The useful surface is at least the portion of outer surfaces of the imaging facility 1, which is exposed during customary operation to potential contamination by the patient and/or an operator. In the present exemplary embodiment, the useful surface comprises at least surfaces of the patient couch 5 and at least portions of the outer surface of the housing unit 2, in particular the front surface with the operator facilities 7 and the wall of the patient receptacle 3.

Apart from the at least one projection facility 13, further output means 12 (not shown here) of the cleaning system can of course also be present, for example display layers provided on and/or below the useful surface, which can be formed, for example, by OLEDs. The projection facility 13 and display layers of this kind enable a space-resolved display of contaminated regions on the useful surface and should be referred to collectively as display facilities. Acoustic and/or haptic output means are conceivable as further output means 12; furthermore, in the present case the touchscreens of the operator facilities 7 can also be operated as presentation facilities 14 of the cleaning system and thus output means 12.

Apart from the cameras 9a, 9b and the microphones 8, further sensors can also be provided in respect of the sensors of the sensor arrangement, for example a temperature sensor for determination of the body temperature of the patient 6, ultrasound sensors, the contact and/or proximity sensors already mentioned and the like.

In the present case, the cameras 9a, 9b are each designed as 3D cameras, provide depth information as well, therefore. In addition, at least one of the cameras is designed as an infrared camera/thermal image camera.

As already indicated in the case of the touchscreens of the operator facilities 14, elements of the cleaning system can also be used in the imaging facility 1 for other purposes. For example, the microphones 8 can also serve for communication with the patient 6, the cameras 9a, 9b and likewise the microphones 8 can serve for monitoring and/or scanning of the patient, for example in respect of movements and the position during the examination procedure, and the like. In particular the cleaning system can use components already present in the imaging facility 1, therefore.

Returning to FIG. 1, a utilization phase of the imaging facility 1 begins in a step S1. During this utilization phase sensor data of the various sensors of the sensor arrangement of the cleaning system, in the present case in particular the cameras 9a, 9b and the microphones 8 therefore, is acquired in a step S2. This sensor data is evaluated in a step S3 in order to identify potentially contaminated regions of the useful surface and to mark them in a surface map of the useful surface. Different approaches are used cumulatively in the framework of this exemplary embodiment to be able to establish and follow contaminations of the useful surface as extensively as possible. Approaches from artificial intelligence can also be used at different locations, in particular in the evaluation of sensor data of the cameras 9a, 9b, for example for the detection of people, the identification of their body parts and the like; this is not imperative, however.

In a first approach, sensor data of the cameras 9a, 9b is principally evaluated by means of at least one image processing algorithm to detect people situated in the room of the imaging facility 1 and to track them at least partially. Such people can be, for example, at least one operator and/or the patient 6. Since 3D cameras 9a, 9b are used, and thus depth information is available, it is possible to establish which regions of the useful surface are contacted by hands and/or other body parts of detected and tracked people. Such regions of the useful surface 5 are then marked in the surface map as being contaminated, with a tolerance range around the actually contacted portions, defined for example by a safety margin and/or percentage-wise, expediently also being incorporated in the contaminated region.

It should be noted at this point that, generally, for example a geometry model of the useful surface can be used as a basis for the surface map and for the assignment of coordinates in the sensor data to the useful surface. A geometry model of this kind can also be used for assignment of lower dimensional sensor data to three-dimensional positions, for example when an infrared camera/thermal image camera measuring only two-dimensions is used. The geometry model can be derived, for example, from geometry reference images acquired with the cameras 9a, 9b and which were acquired in the absence of people and additional objects. These geometry reference images describe the three-dimensional geometry of the useful surface and can also be used in the framework of the image processing algorithm, moreover, to detect, by comparison with images currently being acquired, people and/or objects who/which have come along and take account of them accordingly.

As far as the evaluation of image data of the cameras 9a, 9b in the visible spectrum is concerned, a different aspect of the evaluation of the sensor data provides that the head, specifically the face, at least of the patient 6 is at least intermittently tracked, in particular with a period of time spent in the patient receptacle 3, since, in particular in the case of narrower patient receptacles 3, as are customary in magnetic resonance facilities, contamination due to aerosols can also occur due to straightforward respiration processes, but also due to other aerosol generating procedures, without direct contact. For example, at least one criterion can be defined here, on the fulfilment of which a portion of the useful surface affected by the aerosol generating procedure, in particular respiration process, is characterized as a contaminated region. The at least one criterion can evaluate the length of stay of the head/face in a particular position and/or the distance of the head, specifically face, from the portion of the useful surface. The closer the face is to the useful surface and/or the longer it remains in a corresponding position, the greater the aerosol pollution is and thus the greater the probability of contamination can be assumed to be.

It should be noted at this point already that basically by way of the evaluation of the sensor data, a level of contamination is also assigned to each contaminated region, which is registered in the surface map, which describes how severe the contamination is assumed to be. In the exemplary embodiments discussed to now, such a level of contamination can derive for example from a length of contact and/or the distance of the face from the contaminated region and/or length of stay of the head in the corresponding position.

Since at least one of the cameras 9a, 9b is an infrared camera, temperature differences can also be evaluated in a further evaluation algorithm. For example, it can be conceivable to acquire a comparison image with the infrared camera at the beginning of the utilization phase. A temperature difference image can be generated by comparison with a current image. If this is two-dimensional, depth information, for example from the geometry reference image/geometry model and/or from other, registered sensors, in particular cameras 9a, 9b, can be used to locate temperature references also spatially.

If, for example, an operator makes contact with a part of the useful surface, this will heat up. This may be seen as a temperature difference, in particular even after the contact has already ended, so an improved assessment of instances of contact can occur even if the line of sight to the useful surface was temporarily concealed. Furthermore, the level of the temperature difference can make an important contribution to the determination of the level of contamination since, for example, heating is greater with intensive skin/body contact compared to brief contact or brief contact with an item of clothing.

It not just instances of contact that can be established by way of sensor data of the infrared camera, however. It is also conceivable to identify fluids, in particular bodily fluids, for example saliva, blood and the like, which undesirably contaminate portions of the useful surface. Here too contamination can be established in corresponding regions therefore and be added to the surface map.

An expedient embodiment in respect of the black light facility 10 should also be mentioned in this connection since with illumination using black light, contaminating bodily fluids, in particular also aerosols, glow and are visible in the corresponding sensor data of the cameras 9a, 9b, which was acquired during operation of the black light facility 10. Clear indications of contamination also result herefrom, which are preferably used as additional information in the framework of the accordingly described embodiment, however.

Because in the present case an aerosol contamination algorithm is also used in the framework of sensor data evaluation, which algorithm detects aerosol generating procedures in the sensor data of the camera by detection of speech and/or sneezing noises and/or coughing noises in the sensor data of the microphones 8 and of, in particular, jerky movements in the head region of a person detected by the camera 9a, 9b, in particular of the patient 6. In the present case, an artificial intelligence trained function is used in the aerosol contamination algorithm and evaluates input data, comprising sensor data of the microphones 8 and the cameras 9a, 9b, by means of a neural network in order to obtain, if present, output data describing at least one aerosol procedure. In addition, further input data can of course also be used, for example sensor data of at least one further sensor of the sensor arrangement, for example of said temperature sensor, evaluation results of sensor data of the sensor arrangement, for example in respect of traces of fluids under black light, and/or state of health information describing the state of health of the patient.

Such items of state of health information, which can be retrieved, for example, from an electronic patient file or the like and/or can be derived from an operator input, can also be beneficially used in other ways. While for the aerosol contamination algorithm the state of health information will primarily determine the risk level, for example with regard to an earlier marking as contaminated and/or in order to increase the level of contamination, and this can, of course, also be applied in the evaluation of the sensor data outside of the aerosol contamination algorithm, state of health information can also be communicated to the at least one operator even before beginning the treatment, so preventative measures can be initiated. Should such state of health information, which indicates a high level of infectiousness of the patient, not be known in advance, even when the operator establishes that the patient is not feeling well, for example also by way of communication by the patient, the operator can make an input, which renders the state of health information accessible. State of health information can also be derived from a measurement of the body temperature of the patient, moreover.

Finally, it is also the case that when the next patient has health problems, which make him more susceptible to infections, more intensive cleaning can be effected by an increase in the risk level as early as in the case of the previous patient.

Returning to the aerosol contamination algorithm, the output data of the trained function can also include a classification of the aerosol generating procedure, for example as sneezing, coughing, speech and the like, and this is extremely expedient when determining a level of contamination, which can, of course, also be output directly as output data. In addition, the output data of the trained function can include data relating to the region contaminated by the aerosol generating procedure, so it is known or can at least be established. For example, it is possible to determine from the direction of the aerosol generating procedure which portions of the useful surface are affected, so the contaminated region can be determined. Sensor data acquired under black light or the evaluation results thereof can be used here as a validation tool.

In other words, whenever the trained function detects, for example, sneezing, coughing or another aerosol generating procedure, the current position of the head of the patient 6, in particular the orientation of their face, can be detected and thus the potentially contaminated region of the useful surface established. In exemplary embodiments it is also conceivable, in particular when the orientation of the face is not established, to mark an entire circumferential portion of the patient receptacle 3 as a contaminated region.

The evaluation results of these different evaluation procedures can be combined, it being possible, in particular, to also combine levels of contamination in order to determine a single value. Reliability values can also be supplied with the different evaluation results in this connection, which values can be taken into account in the combination of the levels of contamination.

According to a step S4, a check is then made as to whether the utilization phase has ended. A utilization phase can be clearly defined as the examination procedure of an individual patient, and this is preferable, or else as a particular time span. Alternatively, it is also possible, moreover, when a particular level of soiling is reached, to declare, dynamically as it were, the utilization phase (on completion of the examination procedure currently running) ended.

If the utilization phase has not yet ended, the method returns to step S2, so over time the different potentially contaminated regions can be aggregated in the surface map.

This shall be explained in more detail in the form of a specific example with reference to FIGS. 3 to 7.

FIG. 3 again shows the imaging facility 1 with the housing unit 2 and the patient couch 5. An operator 15 prepares the imaging facility 1 for the arrival of the patient and makes adjustments to the patient couch 5 therefore, for which a handle is touched by a hand, and this is established by evaluation of the sensor data. A contaminated region 16 is produced in the surface map as a result of this contact.

Figure 4:
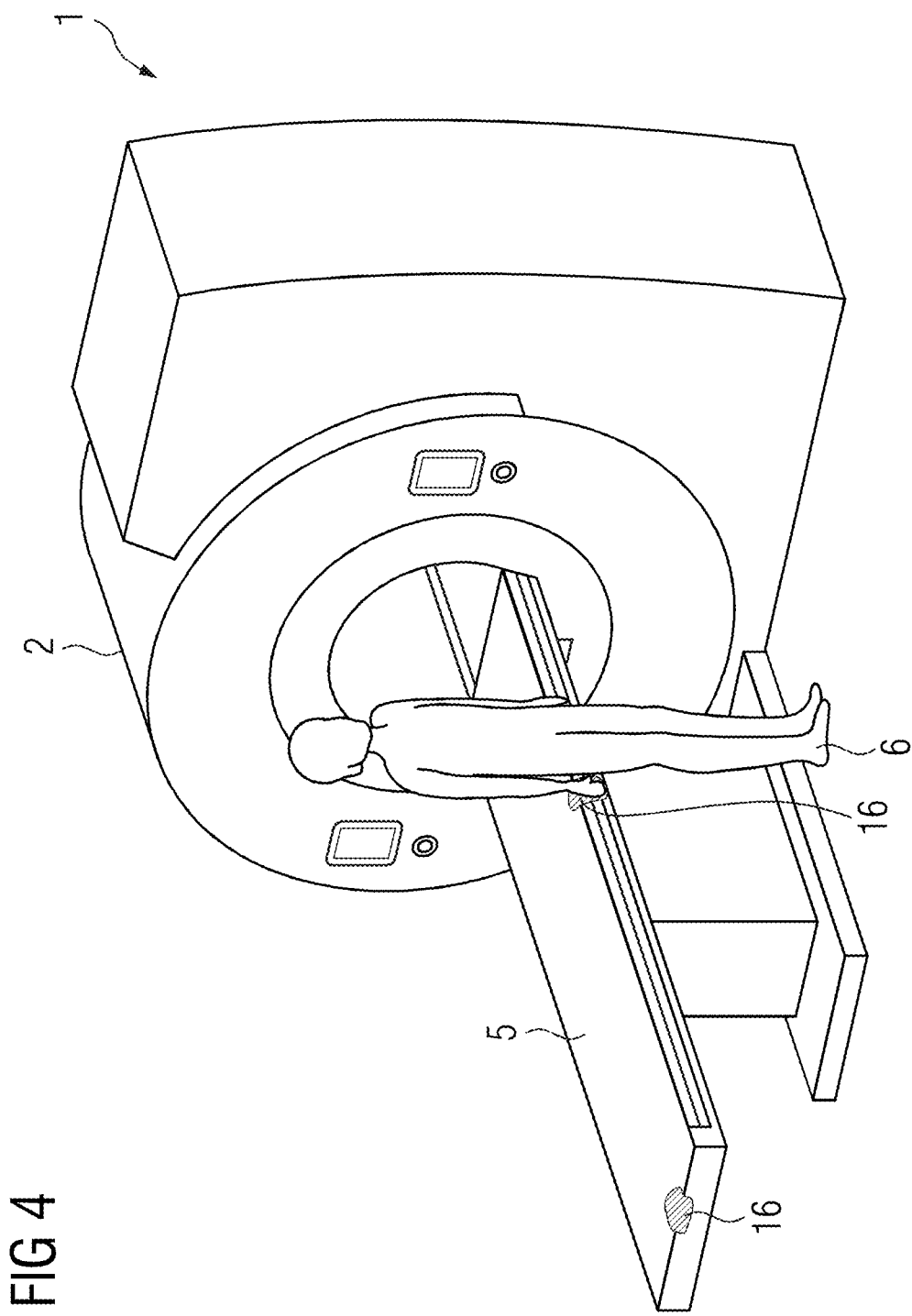
FIG. 4 shows a second situation during a utilization phase.
Figure 5:
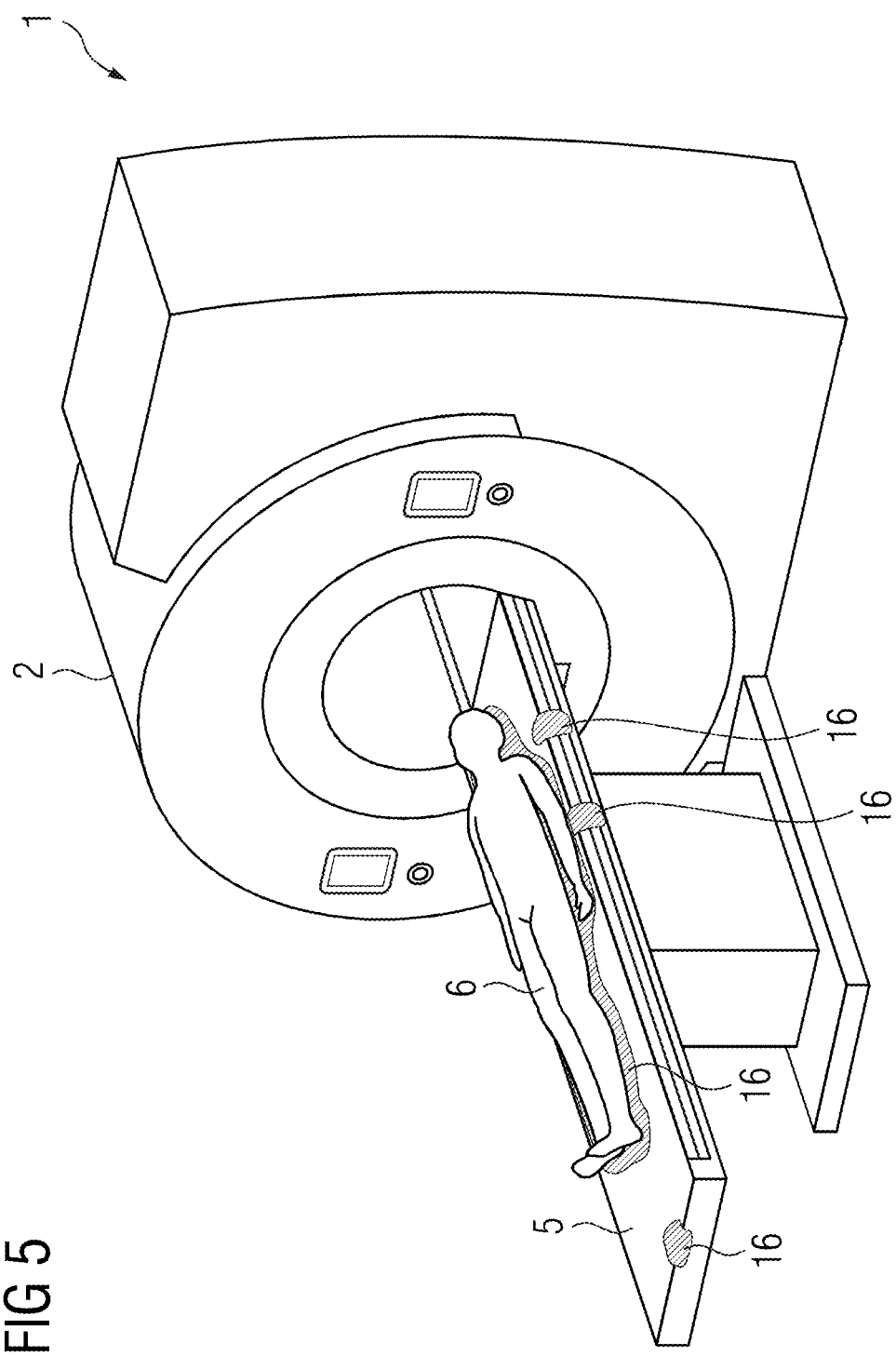
FIG. 5 shows a third situation during a utilization phase.
Figure 6:
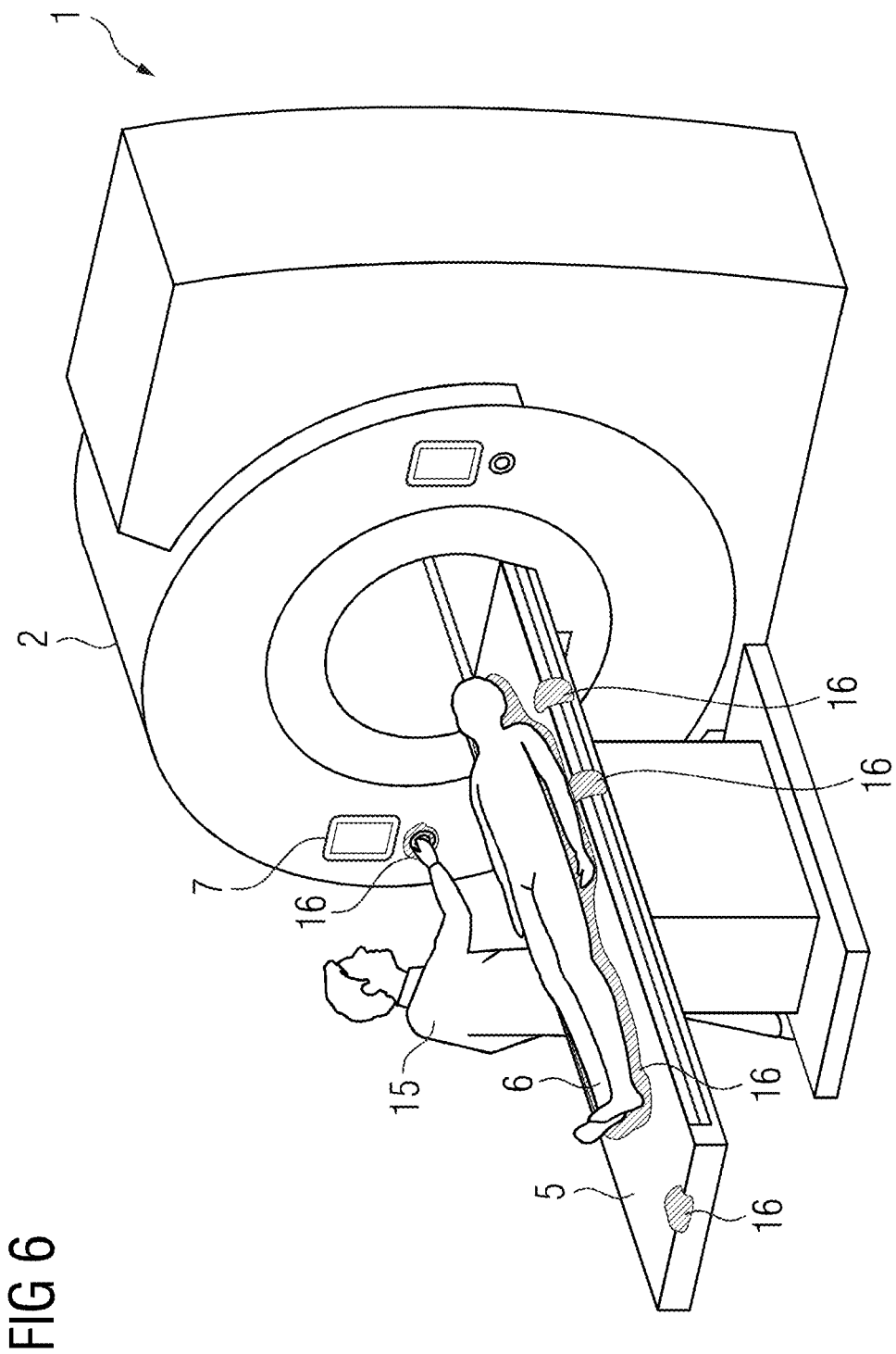
FIG. 6 shows a fourth situation during a utilization phase.

FIG. 4 shows the situation with arrival of the patient 6 who supports himself on the patient couch 5 in order to be seated thereon, and this is in turn detected and results in a further contaminated region 16. In FIG. 5, the patient 6 has then laid himself on the patient couch 5, made large-scale contact with it therefore, and this results in an extended contaminated region 16.

In FIG. 6, the operator 15 is again in the room and uses the left-hand operator facility 7. Contaminated regions 16 are also produced here as a result of the instances of contact.

Figure 7:
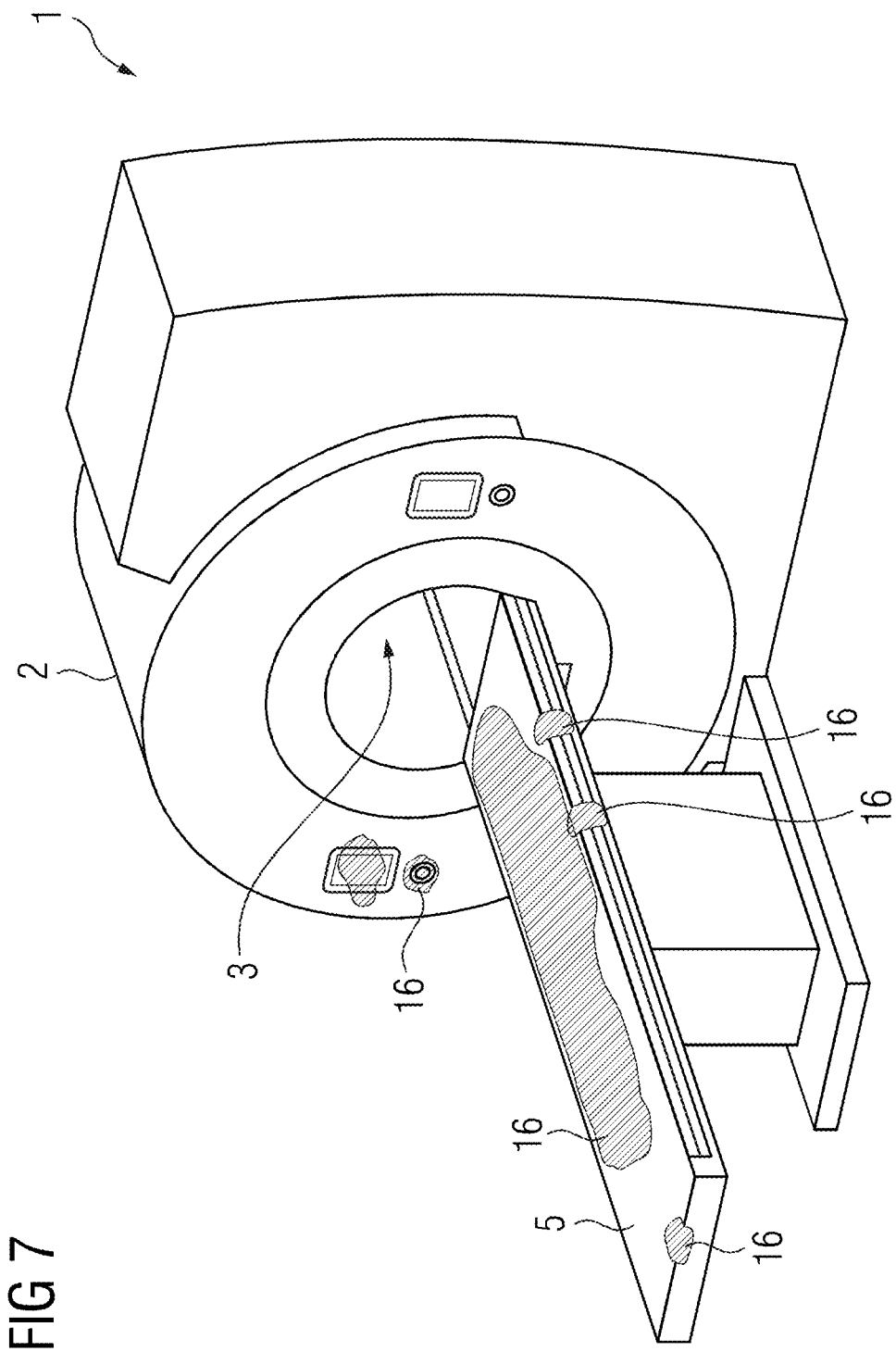
FIG. 7 shows a schematic illustration of a surface map at the completion of the utilization phase.

FIG. 7 shows an exemplary illustration of a resulting surface map for the exemplary case of FIGS. 3 to 6.

Potentially contaminated regions 16 exist both on the patient couch 5 as well as on the portion of the useful surface, which is located on the housing unit 2.

Figure 8:
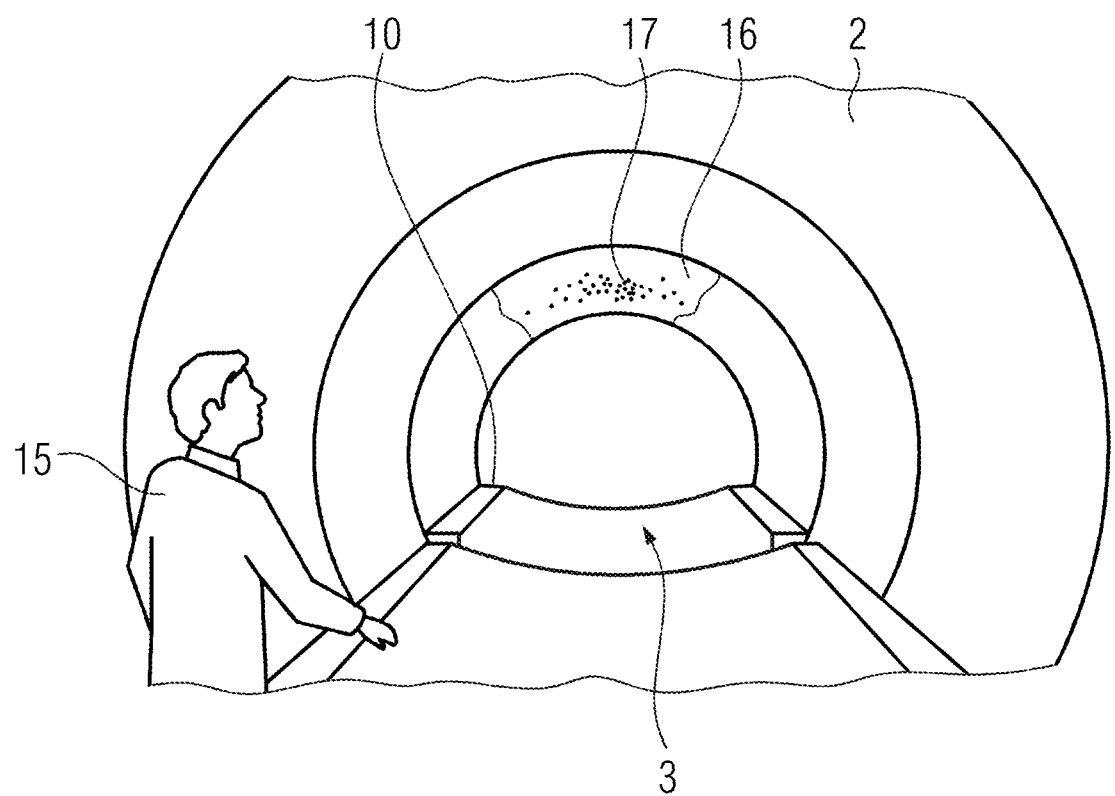
FIG. 8 shows a view into a patient receptacle of the imaging facility.

In addition to the illustration in FIG. 7, FIG. 8 shows a view into the patient receptacle 3 under illumination with black light by means of the black light facility 10. It is evident that a fluid contamination 17 can be seen, which originates from an aerosol generating procedure, for example an act of sneezing or coughing, of the patient 6. Apart from detection in sensor data of the cameras 9a, 9b under black light, an aerosol generating procedure of this kind and an associated contaminated region 16 are established by means of the aerosol contamination algorithm, which comprises the artificial intelligence trained function.

A cleaning phase begins in step S5 after the end of the utilization phase. For this purpose, the imaging facility 1 can be brought into a specific cleaning operating mode in which, for example, components of the imaging facility 1, for example the patient couch 5, assume pre-defined positions, which enable optimum cleaning. In step S5, cleaning information is compiled, which contains at least the contaminated regions 16 of the surface map. In the present exemplary embodiment, a check is also made in step S5, however, as to whether additional information should be added. Such additional information is possibly to be added, for example when the instant for a particular cleaning protocol, which is to be carried out anyway, has arrived, for example end-of-day cleaning, weekend cleaning or even deep cleaning, wherein the corresponding cleaning protocol, which can comprise further areas to be cleaned and associated cleaning factors, is merged, as it were, with the surface map. Depending on the level of contamination, which is assigned to the contaminated regions 16 of the surface map, treatment information can be added to at least some of the contaminated regions 16, moreover, which information can include, for example, cleaning instructions such as a cleaning agent to be used and the like.

Figure 9:
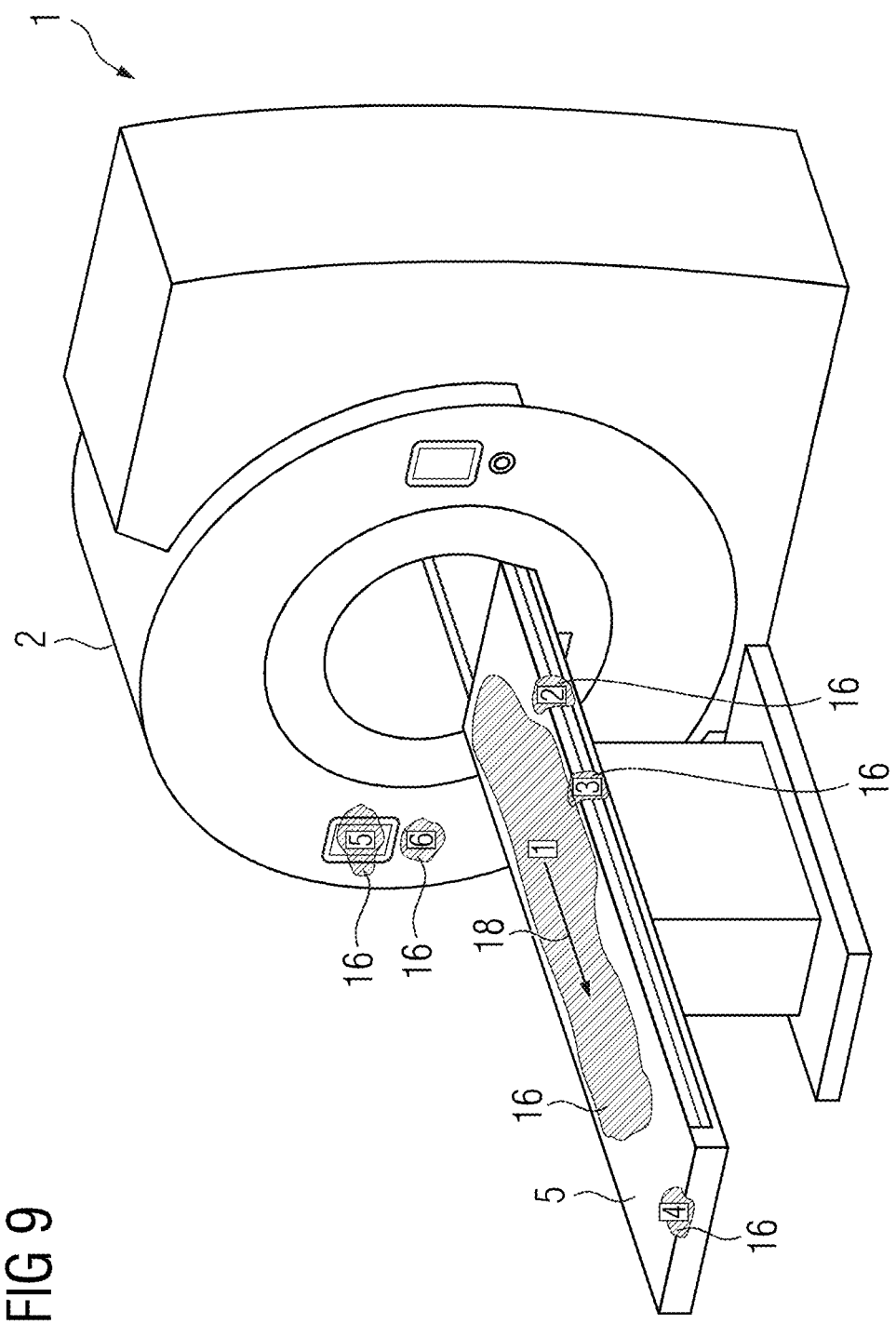
FIG. 9 shows one possible output of cleaning information.

A cleaning workflow is also determined in step S5. The cleaning workflow can comprise, for example, an order of the contaminated regions 16 to be processed and/or a type of processing thereof, for example a wiping direction. FIG. 9 schematically illustrates an exemplary cleaning workflow on the basis of the surface map in FIG. 7. Accordingly, first of all the contamination region 16, in which the patient 6 lay on the patient couch 5, marked "1", should be cleaned with a particular wiping direction, indicated by an arrow 18. The contaminated regions 16, at which the patient supported themselves, marked "2" and "3", in the direction away from the housing unit 2 follow thereafter. The contamination region 16, marked "4", which is furthest away from the housing unit 2 and was contacted by the operator 15 before the arrival of the patient, should then be cleaned. Finally, contamination regions 16, marked "5" and "6", should be cleaned owing to the activity of the operator 15. As described, treatment information, for example cleaning agents to be used, cleaning methods and the like, can also be assigned in the cleaning workflow to the individual contaminated regions 16 that are to be cleaned one after the other.

In a step S6, cf. FIG. 1 again, the cleaning information is output to a cleaner. This takes place by means of the output means 12 already mentioned, in that color superimpositions are projected, for example by means of the projection facilities 13, onto the useful surface where the contaminated regions 16 are located, with it being possible for the manifestation in FIG. 9, for example, to result. The color is selected dependent on the level of contamination. This means that additional information and/or treatment information can of course also be projected in a space-resolved manner onto the useful surface by means of the projection facility 13. Such a space-resolved presentation is also possible in the case of display layers. The level of contamination can also be displayed, for example, by way of a corresponding color selection, which can extend in contaminated regions 16 for example from yellow to dark red. The other described output means 12 can also be used, for example, for an acoustic output of additional information and/or treatment information, a presentation on the presentation facilities 14 and the like.

Figure 10:
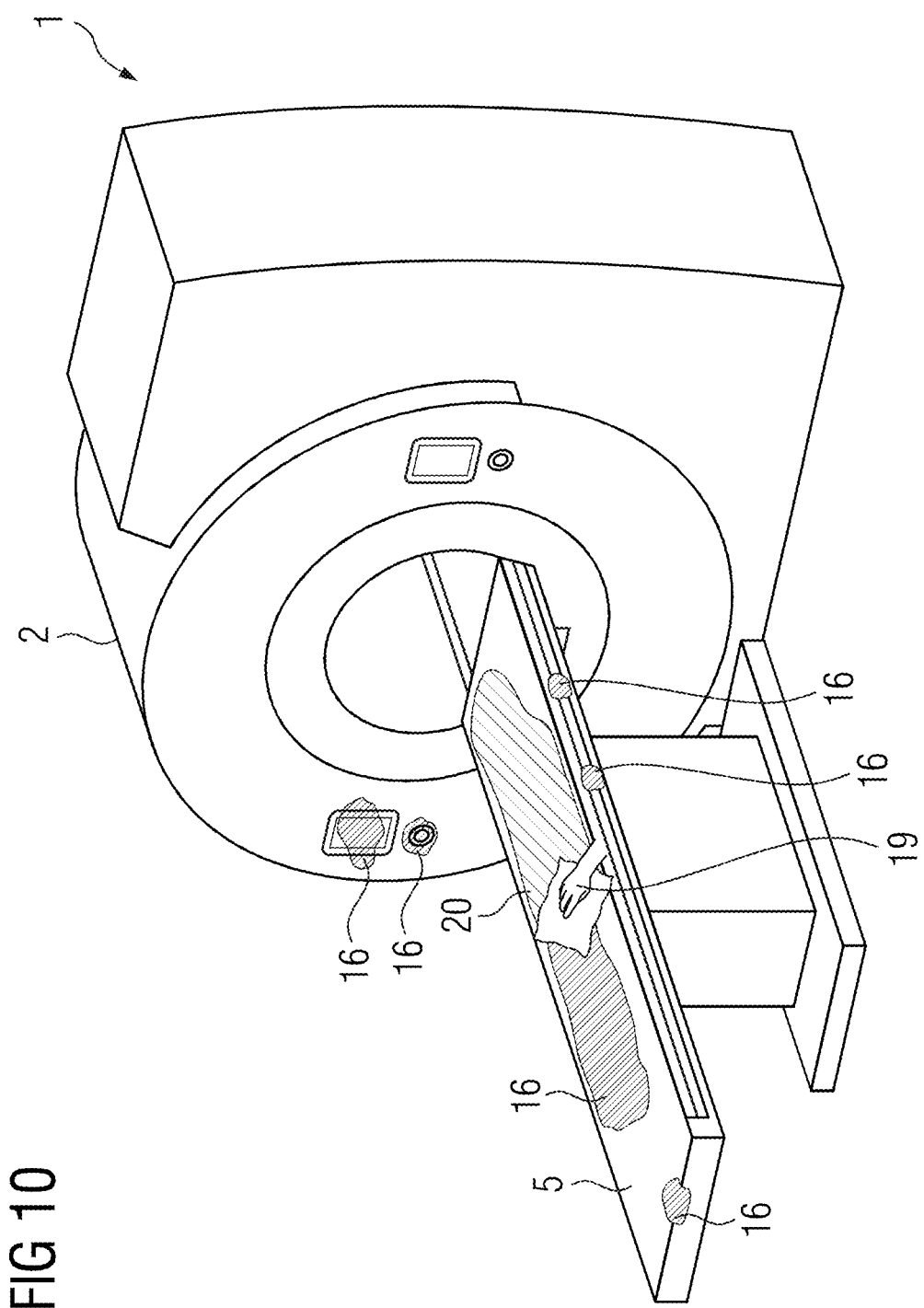
FIG. 10 shows a situation during a cleaning phase.

This output can change dynamically over time since in a step S7 the cleaning process is monitored by means of the sensor arrangement simultaneously and in interaction with step S6. For example, sensor data of the cameras 9a, 9b is evaluated to establish how and where the cleaner cleans. Monitoring information describing the performance and the result of cleaning measures is determined hereby. Processing information and/or results information in respect of this cleaning can be determined for each contaminated region 16, with the output of the cleaning information being adjusted as a function of this processing/results information. This is shown by way of example in FIG. 10, where, as indicated by the illustrated cleaning hand 19, a portion 20 of the contaminated region 16 on the patient couch 5 has already been cleaned. The portion 20 can then be presented for example in green, so the result of the cleaning measure is immediately evident to the cleaner. Furthermore, the cleaner can thus be alerted to portions that have not yet been sufficiently dealt with and prepared.

Once all contaminated regions 16 (and possibly further regions determined by a cleaning protocol) have been cleaned, completion information is determined as monitoring information, and this is likewise output, and, more precisely, both on completion of the cleaning phase as well as at the beginning of the next utilization phase in order to inform the patient 6 there about the effective preparation.

The cleaning information, the monitoring information and the completion information are stored for logging purposes and subsequent evaluation in order, for example, to enable a statistical evaluation with regard to the optimization of products and procedures.

According to FIG. 1, a check is made in a step S8 as to whether the completion information is present. If the cleaning has been completed correctly, apart from the archiving of the information already described, the corresponding indication of results, also follows in step S9.

Figure 11:
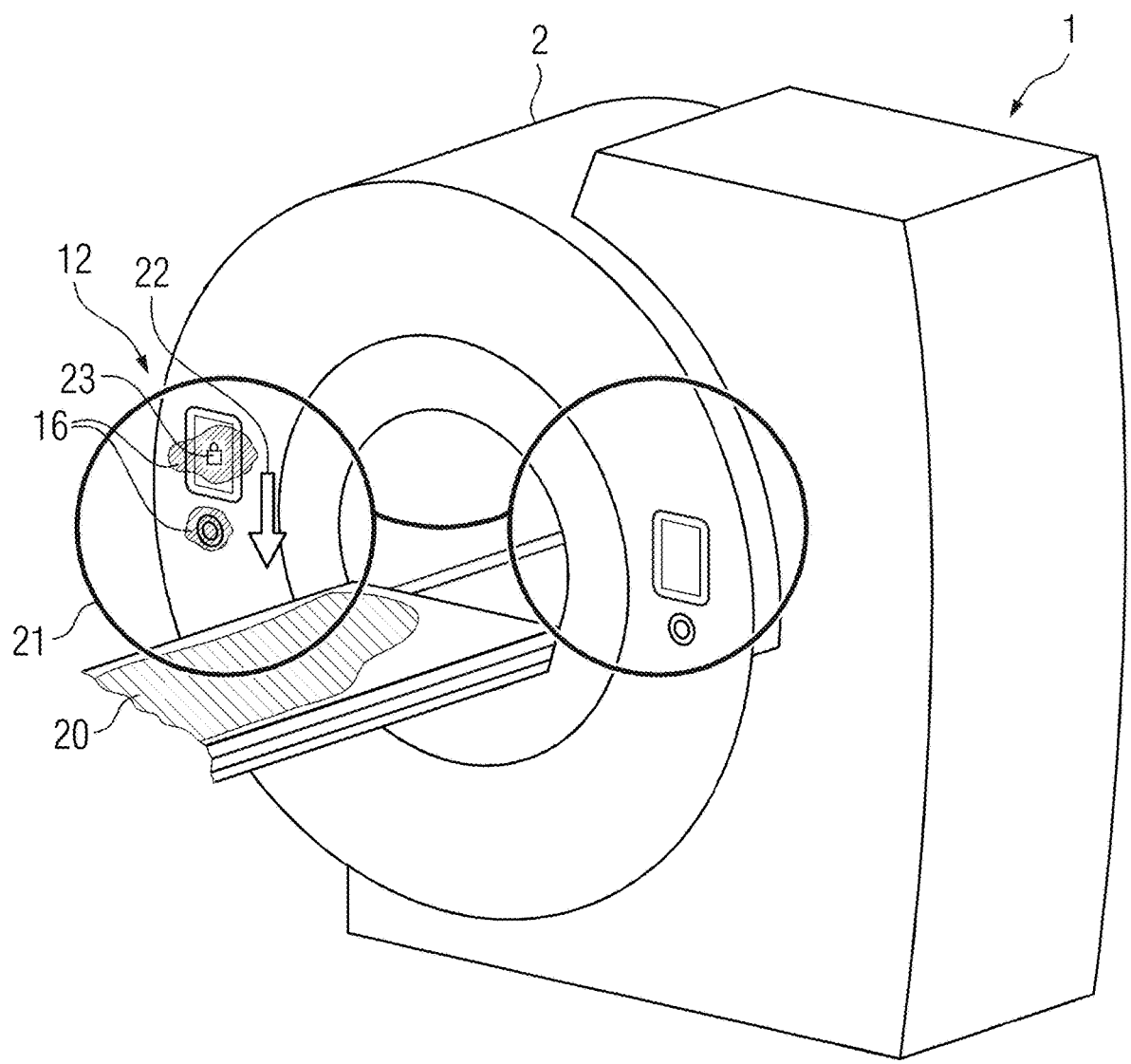
FIG. 11 shows a display in augmented reality glasses.

As FIG. 11 shows, an augmented reality facility, here augmented reality glasses 21, can also be used as an output means 12. With the aid of the augmented reality glasses 21 it is possible to output not just contaminated regions 16 in a contact-analogous manner, but, in addition or alternatively, also additional information and/or treatment information, here by way of example again an arrow 22 to indicate the wiping direction, a symbol 23 to indicate that the touchscreen must be "locked". The output of text, for example for the use of particular cleaning agents and/or cleaning methods, for assignment to a contaminated region 16 is possible.

Figure 12:
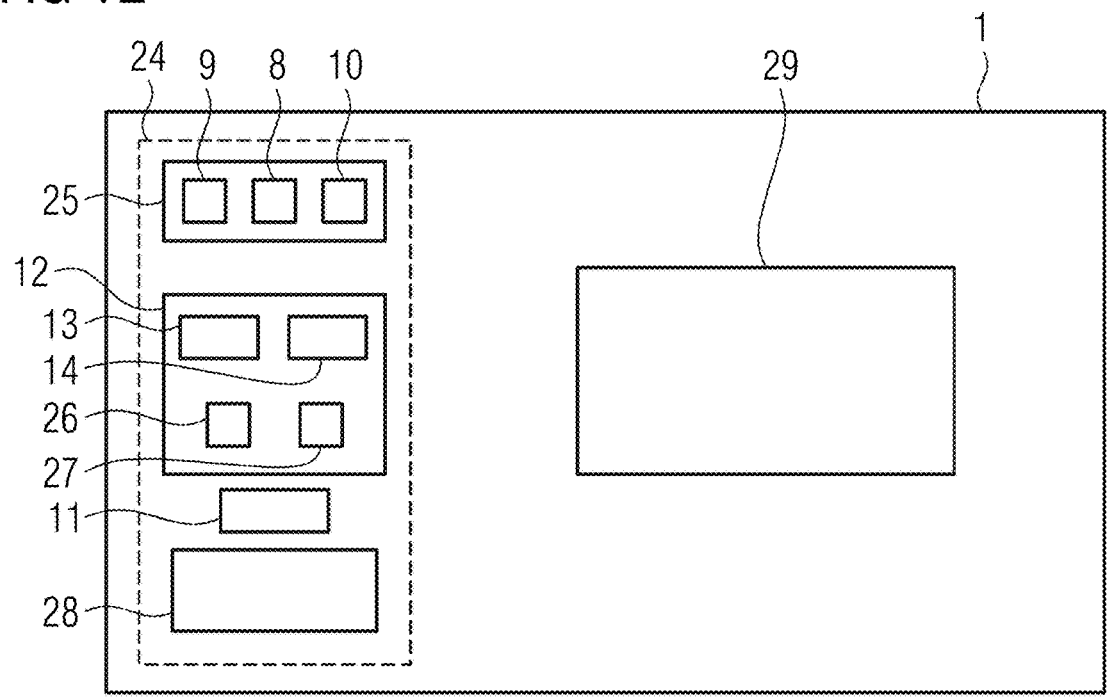
FIG. 12 shows schematic components of the inventive imaging facility.

FIG. 12 is a functional illustration of the inventive imaging facility 1. As already described, this comprises the cleaning system 24 of which the sensor arrangement 25 with the cameras 9, the microphones 8 and possibly further sensors 10 forms a part. Apart from the temperature sensor already mentioned, further sensors 10 can also comprise, for example, contact and/or proximity sensors, for example as films, on at least some of the useful surface.

The output means 12, in particular comprising the projection facilities 13, possibly display layers, the presentation facilities 14 and at least one acoustic output means 26 and at least one haptic output means 27, which can also be used to display effective cleaning, moreover, also form part of the cleaning system 24.

Operation of the cleaning system 24 is controlled by a control facility 28, which is also designed to carry out the inventive method.

Since in the cleaning phase, apart from the cleaning by a cleaner, cleaning apparatuses 11, for example the black light facility 10, automatic cleaning robots and the like, can also be actuated completely automatically, they should also be understood as part of the cleaning system 24.

In the present case, the control facility 28 is also a general control facility for the imaging facility 1, however, which is also designed therefore for the actuation of further components 29 of the imaging facility 1, used in particular for imaging, as the multiple use was already described for other elements of the cleaning system 24, for example the sensor arrangement 25, the presentation facilities 14 and the like.

Figure 13:
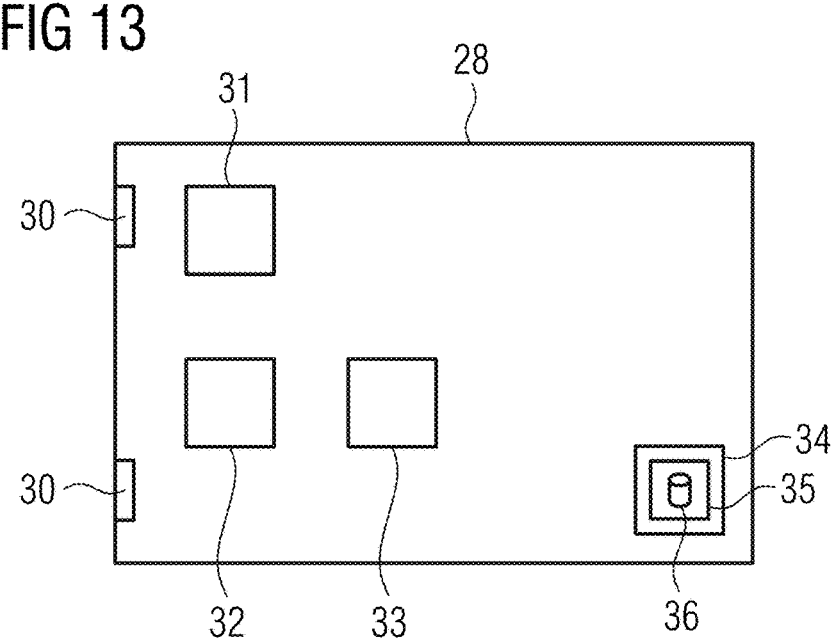
FIG. 13 shows the functional construction of a control facility.

Finally, FIG. 13 shows in a schematically simplified manner the functional construction of the control facility 28 with regard to the cleaning system 24. The control facility 28 firstly has interfaces 30 for the sensor arrangement 25 and the output means 12 as well as the cleaning apparatuses 11.

Of course, further interfaces can also be available for communication with other facilities and/or control of other facilities.

The sensor data of the sensor arrangement 25 is evaluated in an evaluation unit 31 to determine the surface map, the contaminated regions 16 with their levels of contamination and possibly further information, therefore (cf. steps S2 and S3).

The cleaning phase is controlled, in particular the compilation and output of the cleaning information therefore, in a preparation unit 32 in steps S5 and S6. A monitoring unit 33 can be provided for carrying out step S7, the monitoring, therefore. Of course, further function units for carrying out further steps are basically conceivable, for example for the acquisition of comparison and/or geometry reference images and/or for the creation of the geometry model, for the determination of additional information, for example of the state of health information of the patient, and the like.

The control facility 28 can implement the function units (evaluation unit 31, preparation unit 32 and monitoring unit 33 and possibly further function units) for example by means of at least one processor. It also has a storage means 34 in which, inter alia, the cleaning information 35 can be stored with the surface map 36. Algorithms that are used and/or their parameterizations can also be archived and stored in the storage means 34.

Since the control facility 28 also serves to control the rest of the imaging facility 1, it can also contain function units in this regard, for example an acquisition unit for the acquisition of image data sets with the imaging facility 1 and the like.

Although the subject matter of the disclosure has been illustrated and described in detail by the preferred exemplary embodiment it is not limited by the disclosed examples and a person skilled in the art can derive other variations herefrom without departing from the scope of the disclosure.

The invention claimed is:

1. A computer-implemented method for operating a cleaning system of a medical imaging facility, wherein the medical imaging facility has an outer usable surface exposed to contaminating effects of patients and/or operators, the method comprising:
during a utilization phase for an examination procedure of a patient,
acquiring sensor data of a sensor arrangement detecting at least a portion of the usable surface, wherein the sensor arrangement comprises at least one 3D camera and/or at least one microphone; and
determining, by evaluation of the sensor data, a surface map having potentially contaminated regions of the usable surface, wherein for the determination of the surface map during the utilization phase by an image processing algorithm, which evaluates the sensor data of the 3D camera, instances of contact with the usable surface made by a current patient and/or a current operator and/or aerosol generating procedures related to respiration processes are detected, wherein contacted regions of the usable surface and/or regions affected by the aerosol generating procedures are marked as contaminated regions, wherein for the detection of respiration processes relating to aerosol pollution of the usable surface, the method comprises carrying out a patent head tracking process, and wherein aerosol pollution relevant to head positions is detected as a function of a distance of a face of the patient head from the usable surface and/or a length of stay in a position of the patient head; and
during a cleaning phase following the utilization phase,
outputting cleaning information of the potentially contaminated regions to a cleaner; and/or
using the cleaning information of the potentially contaminated regions for actuation of at least one cleaning apparatus of the imaging facility for targeted cleaning of the potentially contaminated regions.

2. The method as claimed in claim 1, wherein the imaging facility is a computed tomography facility or a magnetic resonance facility, and/or has a housing with a patient receptacle into which the patient is movable by means of a patient couch and/or by movement of the housing, wherein at least a portion of the surface of the housing and/or the patient couch is the usable surface.

3. The method as claimed in claim 1, wherein the sensor arrangement comprises at least one 3D camera and/or at least one microphone.

4. The method as claimed in claim 3, wherein for the determination of the surface map during the utilization phase by an image processing algorithm, which evaluates the sensor data of the 3D camera, instances of contact with the usable surface made by a current patient and/or a current operator and/or aerosol generating procedures related to respiration processes are detected, wherein contacted regions of the usable surface and/or regions affected by the aerosol generating procedures are marked as contaminated regions.

5. The method as claimed in claim 4, wherein for the detection of respiration processes relating to aerosol pollution of the usable surface, the method comprises carrying out a patent head tracking process, wherein aerosol pollution relevant to head positions is detected as a function of a distance of a face of the patient head from the usable surface and/or a length of stay in a position of the patient head.

6. The method as claimed in claim 4, wherein at least a portion of the sensor data of the camera is acquired by illumination of at least a portion of the usable surface with black light and/or by means of a UV irradiation facility also used as a cleaning apparatus, wherein in the evaluation of the sensor data, regions of the usable surface glowing under the illumination are detected as being at least partially contaminated.

7. The method as claimed in claim 4, wherein at least one of the at least one cameras is an infrared camera, and instances of contact are detected on the basis of a temperature difference of a current image from at least one previously acquired image on completion of its cleaning phase, wherein a comparison image comprises temperature information.

8. A computer-implemented method for operating a cleaning system of a medical imaging facility, wherein the medical imaging facility has an outer usable surface exposed to contaminating effects of patients and/or operators, the method comprising:
during a utilization phase for an examination procedure of a patient,
acquiring sensor data of a sensor arrangement detecting at least a portion of the usable surface, wherein the sensor arrangement comprises at least one 3D camera and/or at least one microphone, wherein at least one of the at least one cameras is an infrared camera, and instances of contact are detected on the basis of a temperature difference of a current image from at least one previously acquired image on completion of its cleaning phase, and wherein a comparison image comprises temperature information; and determining, by evaluation of the sensor data, a surface map having potentially contaminated regions of the usable surface, wherein for the determination of the surface map during the utilization phase by an image processing algorithm, which evaluates the sensor data of the 3D camera, instances of contact with the usable surface made by a current patient and/or a current operator and/or aerosol generating procedures related to respiration processes are detected, wherein contacted regions of the usable surface and/or regions affected by the aerosol generating procedures are marked as contaminated regions, wherein in addition to instances of contact, presence of bodily fluids on the usable surface is detected using the temperature difference, and wherein regions of the usable surface having bodily fluids are also marked as contaminated; and during a cleaning phase following the utilization phase,
outputting cleaning information of the potentially contaminated regions to a cleaner; and/or
using the cleaning information of the potentially contaminated regions for actuation of at least one cleaning apparatus of the imaging facility for targeted cleaning of the potentially contaminated regions.

9. A computer-implemented method for operating a cleaning system of a medical imaging facility, wherein the medical imaging facility has an outer usable surface exposed to contaminating effects of patients and/or operators, the method comprising:

during a utilization phase for an examination procedure of a patient,
acquiring sensor data of a sensor arrangement detecting at least a portion of the usable surface, wherein the sensor arrangement comprises at least one 3D camera and/or at least one microphone, wherein at least one of the at least one cameras is an infrared camera, and instances of contact are detected on the basis of a temperature difference of a current image from at least one previously acquired image on completion of its cleaning phase, and wherein a comparison image comprises temperature information;

determining, by evaluation of the sensor data, a surface map having potentially contaminated regions of the usable surface, wherein for the determination of the surface map during the utilization phase by an image processing algorithm, which evaluates the sensor data of the 3D camera, instances of contact with the usable surface made by a current patient and/or a current operator and/or aerosol generating procedures related to respiration processes are detected, wherein contacted regions of the usable surface and/or regions affected by the aerosol generating procedures are marked as contaminated regions; and wherein without the presence of people and additional objects in a field of view of the at least one camera, together with the comparison image, acquiring a geometry reference image, which describes a three-dimensional geometry comprising a three-dimensional course of the usable surface, wherein by forming difference images of the geometry reference image with at least one currently acquired image, the people and/or objects obscuring the usable surface are detected and taken into account when determining contaminated regions; and during a cleaning phase following the utilization phase,
outputting cleaning information of the potentially contaminated regions to a cleaner; and/or
using the cleaning information of the potentially contaminated regions for actuation of at least one cleaning apparatus of the imaging facility for targeted cleaning of the potentially contaminated regions.

10. The method as claimed in claim 3, wherein during the course of the sensor data evaluation by an aerosol contamination algorithm, by detection of speech and/or sneezing noises and/or coughing noises in the sensor data of the microphone and/or of jerky movements in the head region of a person detected by the camera in the sensor data of the camera, the method further comprises detecting aerosol generating procedures, wherein regions of the usable surface affected by a detected aerosol generating procedure are marked as contaminated.

11. The method as claimed in claim 10, wherein the aerosol contamination algorithm comprises an artificial intelligence trained function, wherein the trained function is applied to input data comprising sensor data of the microphone and/or the camera to obtain output data describing the existence of at least one aerosol generating procedure.

12. The method as claimed in claim 11, wherein the input data comprises sensor data of at least one further sensor of the sensor arrangement and/or at least one evaluation result of sensor data of the sensor arrangement in respect of an illumination with UV light, and/or state of health information describing the state of health of the patient.

13. The method as claimed in claim 11, wherein the output data comprises a classification of the aerosol generating procedure and/or the region contaminated by the aerosol generating procedure and/or information comprising a severity level of the contamination.

14. The method as claimed in claim 1, wherein on evaluation of the sensor data, the method further comprises determining a level of contamination describing the severity of the contamination, which is taken into account in the selection of the contaminating regions to be output and/or is output with information of the contaminated regions and/or is used for selection of treatment information to be output with the information of the contaminated regions.

15. The method as claimed in claim 1, wherein at least one item of a cleaning protocol and/or dependent on the instant of the beginning of the cleaning phase, is added to the cleaning information at the beginning of the cleaning phase.

16. The method as claimed in claim 1, wherein the contaminated regions and/or further regions of the usable surface contained in the cleaning information as ones to be cleaned, are visualized in a space-resolved manner by means of a display facility.

17. The method as claimed in claim 16, wherein at least one projection facility and/or an OLED layer provided on and/or below the usable surface is used as the display facility and/or the space-resolved display, and on determination of a level of contamination, is configured to display the level of contamination and/or the treatment information.

18. The method as claimed in claim 1, wherein the cleaning information is output at least partially acoustically and/or haptically and/or by means of a presentation facility provided in addition to the display facility, and/or the cleaning information is output at least partially using an augmented reality glasses and/or in a contact-analogous manner.

19. The method as claimed in claim 1, wherein the sensor arrangement is also operated during the cleaning phase for the acquisition of sensor data, which is evaluated for determination of an item of monitoring information describing the implementation and/or the result of cleaning measures.

20. The method as claimed in claim 19, wherein processing and/or results information in respect of each contaminated region is determined as the monitoring information for cleaning thereof, wherein the output of the contaminated region is changed in order to display processing and/or effective cleaning thereof, and/or that completion information indicating the completion of all cleaning measures is determined as the monitoring information, and this is likewise output on completion of the cleaning phase and/or at the beginning of the next utilization phase.

21. An imaging facility, comprising:
   a cleaning system with a sensor arrangement; and
   a control facility configured to carry out the method as claimed in claim 1.

22. A non-transitory computer readable medium having stored thereon a computer program, which carries out the steps of the method as claimed in claim 1 when run on a control facility of a cleaning system of an imaging facility.

* * * * *